(12) United States Patent
Koo et al.

(10) Patent No.: US 11,692,212 B2
(45) Date of Patent: *Jul. 4, 2023

(54) DIAGNOSIS AND TREATMENT OF INVASIVE ASPERGILLOSIS

(71) Applicant: The Brigham and Women's Hospital, Inc., Boston, MA (US)

(72) Inventors: Sophia Koo, Brookline, MA (US); Horatio R. Thomas, Cambridge, MA (US); Lindsey R. Baden, Brookline, MA (US); Francisco M. Marty, Chestnut Hill, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 54 days.

This patent is subject to a terminal disclaimer.

(21) Appl. No.: 17/228,382

(22) Filed: Apr. 12, 2021

(65) Prior Publication Data

US 2022/0049281 A1 Feb. 17, 2022

Related U.S. Application Data

(63) Continuation of application No. 16/298,521, filed on Mar. 11, 2019, now abandoned, which is a
(Continued)

(51) Int. Cl.
*C12Q 1/04* (2006.01)
*G01N 33/497* (2006.01)
(Continued)

(52) U.S. Cl.
CPC ............. *C12Q 1/04* (2013.01); *A61B 5/082* (2013.01); *G01N 33/497* (2013.01); *A61B 5/08* (2013.01);
(Continued)

(58) Field of Classification Search
CPC ........... A61P 31/10; G01N 2033/4975; G01N 2333/38; G01N 33/497; G01N 2800/26;
(Continued)

(56) References Cited

U.S. PATENT DOCUMENTS 7,019,291 B2 3/2006 Miller et al.
7,605,367 B2 10/2009 Miller et al.
(Continued)

FOREIGN PATENT DOCUMENTS

WO WO 2006/112733 10/2006
WO WO 2014/039856 3/2014
WO WO-2014039856 A1 * 3/2014 ........... A61K 31/427

OTHER PUBLICATIONS

Koo et al., (53rd ICAAC Sep. 10-13, 2013, Denver CO. Control/Tracking No. 2013-A-2373-ASM-ICAAC) i (Year: 2013).*
(Continued)

*Primary Examiner* — Jana A Hines
(74) *Attorney, Agent, or Firm* — Fish & Richardson P.C.

(57) ABSTRACT

Methods for diagnosing, treating, and monitoring the treatment of invasive aspergillosis (IA) are described. The methods can include detecting the presence of one or more volatile organic compounds (VOCs) in the breath of subjects suspected of having IA.

10 Claims, 19 Drawing Sheets

Related U.S. Application Data continuation of application No. 15/316,062, filed as application No. PCT/US2015/034182 on Jun. 4, 2015, now Pat. No. 10,227,629.

(60) Provisional application No. 62/050,583, filed on Sep. 15, 2014, provisional application No. 62/008,419, filed on Jun. 5, 2014.

(51) Int. Cl.
A61B 5/08 (2006.01)
A61B 5/145 (2006.01)

(52) U.S. Cl.
CPC .. A61B 5/14546 (2013.01); G01N 2033/4975 (2013.01); G01N 2333/38 (2013.01); G01N 2800/18 (2013.01); G01N 2800/26 (2013.01); G01N 2800/52 (2013.01)

(58) Field of Classification Search
CPC .. G01N 2800/18; G01N 2800/52; A61B 5/08; A61B 5/14546; A61B 5/082; C12Q 1/04
See application file for complete search history.

(56) References Cited

U.S. PATENT DOCUMENTS

| | | |
|---|---|---|
| 8,481,789 B2 | 7/2013 | Mane |
| 10,031,125 B2 | 7/2018 | Koo et al. |
| 10,227,629 B2 | 3/2019 | Koo et al. |
| 2004/0092583 A1 | 5/2004 | Shanahan-Prendergast |
| 2007/0003996 A1 | 1/2007 | Hitt et al. |
| 2008/0286830 A1* | 11/2008 | Scotter .............. C12Q 1/04 435/34 |
| 2009/0078865 A1 | 3/2009 | Zapata et al. |
| 2009/0308136 A1 | 12/2009 | Wang et al. |
| 2010/0291617 A1 | 11/2010 | Trevejo et al. |
| 2013/0168548 A1 | 7/2013 | Wang et al. |
| 2015/0233895 A1 | 8/2015 | Koo et al. |
| 2019/0203256 A1 | 7/2019 | Koo et al. |
| 2021/0239680 A1 | 8/2021 | Koo et al. |

OTHER PUBLICATIONS

Takeuchi et al (Surf Interface Anal. Mar. 2012, 44, pp. 694-698), (Year: 2012).*
Polizzi et al (Fungal Biology, Jun. 2012, vol. 116, pp. 941-953). (Year: 2012).*
U.S. Appl. No. 61/698,155, filed Sep. 7, 2012, Koo et al.
Absrtactonline.com [online] "Final Program 52nd Interscience Conference on Antimicrobial Agents and Chemotherapy Sep. 9-12, 2012," Sep. 9-12, 2012, [retrieved on Mar. 24, 2016]. Retrieved from the internet: URL:http://www.asm.org/images/ICAAC 2012 FinalProgram Web4a.pdf , pp. 340-341.
Absrtactonline.com [online] Oasis Product Development Team, "Online Program Planner for the 52nd ICACC—Sep. 9-12—San Francisco," Sep. 9-12, 2012, [retrieved on Mar. 24, 2016]. Retrieved from the internet: URL:http://www.abstractsonline.com/plan/start.aspx?mkey=%7B6B114A1D-85A4-4054-A83B-O4D8B9B8749F%7D.
Abstractonline.com [online] S. Koo et.al, "Breath Volatile organic compound (VOC) Profiles for the Diagnosis of Invasive Aspergillosis (IA)," Online Meeting Planner for the 52nd Interscience Conference on Antimicrobial Agents and Chemotherapy (ICACC), Sep. 9-12, 2012, Aug. 9, 2012 [Retrieved on Mar. 24, 2016]. Retrieved from the internet: URL:http://www.abstractsonline.com/Plan/View Abstract.aspx?sKey=50e8c5eb-47e8-4e58-ed2-720d86b384f9&cKey=4920b27b-9cdd-4db3-822d-69b73708fc7c&mKey=%7b6B114A1D-85A4-4054-A83B-04D8B9B8749F%7d.
Baddley et al., "Patterns of susceptibility of Aspergillus isolates recovered from patients enrolled in the Transplant-Associated Infection Surveillance Network," J Clin Microbiol., Oct. 2009;47(10): 3271-5.
Balajee et al., "Molecular identification of Aspergillus species collected for the Transplant-Associated Infection Surveillance Network," J Clin Microbiol., Oct. 2009. 47: 3138-3141.
Bazemore et al., Biomedically important, pathogenic fungi detection with volatile biomarkers, Journal of Breath Research, 2012, 6:016002.
Bhandari et al., "Determining the limits and cofounders for the 2-pentyl furan breath test by gas chromatography/mass spectrometry," Journal of Chromatography B: Biomedical Sciences & Applications, 2011, 879(26): 2815-2820.
Brakhage "Regulation of fungal secondary metabolism," Nature Reviews Microbiology, Jan. 2013, 11:21-32.
Cane and Kang, "Aristolochene synthase: purification, molecular cloning, high-level expression in Escherichia coli, and characterization of the Aspergillus terreus cyclase," Archives of Biochemistry and Biophysics, Apr. 2000, 376:354-364.
Chambers et al., "Novel diagnostics: progress toward a breath test for invasive Aspergillus fumigatus," Medical Mycology, 2011, 49(S1): S54-S61.
Chou et al., "Study of the chemical composition, antioxidant activity and anti-inflammatory activity of essential oil from Vetiveria zizanioides," Food Chem., Sep. 2012, 134(1):262-268.
Davis et al., "Spore biomarker detection using a MEMS differential mobility spectrometer," In: 12th International Conference on Transducers, Solid-State Sensors, Actuators and Microsystems; 2003; p. 1233-8 vol. 2.
De Heer et al., "Electronic Nose Technology for Detection of Invasive Pulmonary Aspergillosis in Prolonged Chemotherapy-Induced Neutropenia: a Proof-of-Principle Study," Journal of Clinical Microbiology, Mar. 5, 2013, 51(5): 1490-1495.
De Pauw et al., "Revised definitions of invasive fungal disease from the European Organization for Research and Treatment of Cancer/Invasive Fungal Infections Cooperative Group and the National Institute of Allergy and Infectious Diseases Mycoses Study Group (EORTC/MSG) Consensus Group," Clin Infect Dis., 2008, 46:1813-1821.
EP Office Action in European Appln. No. 15802361, dated Jul. 16, 2020, 4 pages.
European Search Report in Application No. 15802361.4, dated Nov. 3, 2017, 11 pages.
Extended European Search Report in International Application No. PCT/US2013058560, dated Apr. 7, 2016, 9 pages.
Fiedler et al., "Detection of microbial volatile organic compounds (MVOCs) produced by moulds on various materials," Int J Hyg Environ Health, 2001, 204:111-121.
Fischer et al., "Species-specific production of microbial volatile organic compounds (MVOC) by airborne fungi from a compost facility," Chemosphere, Aug. 1999, 39(5):795-810.
Fischer G. et al., "Species-specific production of microbial volatile organic compounds (MVOC) by airborne fungi from a compost facility," Chemosphere 39(5): 795-810 (1999).
Fong et al., "Automated peak detection and matching algorithm for gas chromatography-differential mobility spectrometry," Anal Chem., Mar. 1, 2011;83(5):1537-46 (Author Manuscript).
Frisvad et al., "Metabolomics of Aspergillus fumigatus," Med Mycol., 2009:47: S53-S71.
Goa et al., "Determination of unique microbial volatile organic compounds produced by five Aspergillus species commonly found in problem buildings," AIHAJ: A Journal for the Science of Occupational and Environmental Health and Safety, 202, 62(2): 135-140.
Heddergott et al., "The Volatome of Aspergillus fumigatus," Eukaryotic Cell, Aug. 2014, 13(8): 1014-1025.
Hope et al., "Laboratory diagnosis of invasive aspergillosis." Lancet Infect Dis., Oct. 2005, 5:609-622.
Ibrahim Bin Jantan et al., "Correlation Between Chemical Composition and Antifungal Activity of the Essential Oils of Eight Cinnamomum Species," Pharmaceutical Biology 46 (6): 406-412 (2008).
International Preliminary Report on Patentability in International Application No. PCT/US2013/058560, dated Mar. 10, 2015, 13 pages.

(56) References Cited

OTHER PUBLICATIONS

International Preliminary Report on Patentability in International Application No. PCT/US2015/034182, dated Dec. 6, 2016, 8 pages.
International Search Report and Written Opinion dated Aug. 26, 2015 in international application No. PCT/US2015/34182, 10 pgs.
International Search Report and Written Opinion dated Dec. 26, 2013 in international application No. PCT/US2013/058560, 10 pgs.
Jelen et al., "Volatile compounds of Aspergillus strains with different abilities to produce ochratoxin A," Journal of Agricultural and Food Chemistry, Mar. 2005, 53(5):1678-1683.
Kanu AB et al., "Ion mobility spectrometry detection for gas chromatography," J Chromatogr A., 1177(1): 12-27 (2008), abstract.
Kanu et al., "Ion mobility-mass spectrometry," J Mass Spectrom., Jan. 2008;43(1):1-22.
Karthaus M. Prophylaxis and Treatment of Invasive Aspergillosis with Voriconazole, Posaconazole and Caspofungin Review of the Literature, European Journal of Medical Research 16:145-152 (2011).
Keller et al., "Fungal secondary metabolism—from biochemistry to genomics," Nat Rev Microbiol., Dec. 2005, 3:937-947.
Kolakowski and Mester, "Review of applications of high-field asymmetric waveform ion mobility spectrometry (FAIMS) and differential mobility spectrometry (DMS)," Analyst., Sep. 2007;132(9):842-64.
Koo et al., "A Breath Fungal Secondary Metabolite Signature to Diagnose Invasive Aspergillosis," Clinical Infectious Diseases, Dec. 15, 2014, 59(12): 1733-1740.
Koo et al., "An Aspergillus fumigatus (AF)-specific Breath Volatile Organic Compound (VOC) Profile is Diagnostic of Invasive Aspergillosis (IA)," 53rd ICAAC, Sep. 10-13, 2013, 3 pages.
Koo et al., "Diagnostic performance of the (1-->3)-beta-D-glucan assay for invasive fungal disease," Clin Infect Dis., Dec. 2009. 49(11):1650-1659.
Kramer and Abraham, "Volatile sesquiterpenes from fungi: what are they good for?," Phytochemistry Reviews, 2012, 11:15-37.
Krebs et al., "Detection of Biological and Chemical Agents Using Differential Mobility Spectrometry (DMS) Technology," Sensors Journal, IEEE 2005 5(4):696-703.
Kwak and Preti, "Volatile Disease Biomarkers in Breath: A Critique," Current Pharmaceutical Biotechnology, 2011, 12(7): 1067-1074.
Lin et al., "Identification of Unique Volatile Compounds of Aspergillus fumigatus for Potential Diagnostic Breath Test, by HSSPME and GC-MS," J. Immunol. Tech. Infect. Dis., 2013, 2(3): 1-4.
Lin et al., "The fumagillin biosynthetic gene cluster in Aspergillus fumigatus encodes a cryptic terpene cyclase involved in the formation of β-trans-bergamotene," Journal of the American Chemical Society, Mar. 2013, 135:4616-4619.
Luong et al., "Gas chromatography with state-of-the-art micromachined differential mobility detection: operation and industrial applications," J Chromatogr Sci., May-Jun. 2006;44(5):276-86.
Marr et al., Treatment and prevention of invasive aspergillosis, Up-to-Date (topic updated on Oct. 18, 2012; literature review Aug. 2013; available at http://www.uptodate.com/contents/treatment-and-prevention-of-invasive-aspergillosis?topicKey=ID%2F2459&elapsedTimeMs=7&view=print&displayedView=full, 18 pages.
McDonagh et al., "Sub-telomere directed gene expression during initiation of invasive aspergillosis," PLoS Pathog., Sep. 12, 2008;4(9):e1000154, 21 pages.
Merrick, "Characterization of Human Expired Breath by Solid Phase Microextraction and Analysis Using Gas Chromatography-Mass Spectrometty and Differential Mobility Spectrometry," Thesis Harvard-MIT Division of Health Science and Technology, Aug. 10, 2005, 95 pages.

Milroy et al., "Aspergillosis of the nose and paranasal sinuses," J Clin Pathol., Feb. 1989;42(2):123-7.
Nazarov et al., "Pressure effects in differential mobility spectrometry," Anal Chem., Nov. 15, 2006;78(22):7697-706.
Neofytos et al., "Epidemiology and outcome of invasive fungal infection in adult hematopoietic stem cell transplant recipients: analysis of Multicenter Prospective Antifungal Therapy (PATH) Alliance registry," Clin Infect Dis., Feb. 1, 2009, 48(3):265-273.
Pappas et al., "Invasive fungal infections among organ transplant recipients: results of the Transplant-Associated Infection Surveillance Network (TRANSNET)," Clinical Infectious Diseases, 2010, 50:1101-1111.
Perfect et al., "The impact of culture isolation of *Aspergillus* species: a hospital-based survey of aspergillosis." Clin Infect Dis., 2001, 33:1824-1833.
Pfeiffer CD, Fine JP, Safdar N. Diagnosis of invasive aspergillosis using a galactomannan assay: a meta-analysis. Clin Infect Dis. 2006;42:1417-1427.
Phillips et al., "Prediction of lung cancer using volatile biomarkers in breath 1," Cancer Biomarkers, Jan. 2007, 3(2):95-109.
Polizzi et al., "Identification of volatile markers for indoor fungal growth and chemotaxonomic classification of *Aspergillus* species," Fungal Biology, Jun. 2012, 116(9):941-953.
Polizzi V. et al., "Identification of volatile markers for indoor fungal growth and chemotaxonomic classification of *Aspergillus* species," Fungal biology 116: 941-953 (2012).
Pontecorvo et al., "The genetics of Aspergillus nidulans," Adv Genet. 1953;5:141-238.
Purkhart et al., "Chronic intestinal *Mycobacteria* infection: discrimination via VOC analysis in exhaled breath and headspace of feces using differential ion mobility spectrometry," Journal of Breath Research, 5(2), 2011, p. 027103.
Rath et al., "Differentiation of Aspergillus ustus Strains by Random Amplification of Polymorphic DNA," Journal of Clinical Microbiology, Jun. 2002, 40: 2231-2233.
Reichenberger et al., "Diagnostic yield of bronchoscopy in histologically proven invasive pulmonary aspergillosis." Bone Marrow Transplant, 1999, 24:1195-1199.
Sethi et al., "Clinical application of volatile organic compound analysis for detecting infectious diseases," Clinical Microbiology Reviews, Jul. 2013, 26:462-475.
Shnayderman et at, "Species-specific bacteria identification using differential mobility spectrometry and bioinformatics pattern recognition," Anal Chem., Sep. 15, 2005;77(18):5930-7.
Syhre et al., "Investigation into the production of 2-Pentylfuran by Aspergillus fumigatus and other respiratory pathogens in vitro and human breath samples," Med Mycol., 2008, 46:209-215.
Takeuchi et al., "Analysis of volatile metabolites emitted by soil-derived fungi using head space solid-phase microextraction/gas chromatography/mass spectrometry: I. Aspergillus fumigatus, Aspergillus nidulans, Fusarium solani and Penicillium paneum," Surf. Interface Anal., Mar. 2012, 44(6):694-698.
U.S. Non-Final Office Action in U.S. Appl. No. 14/426,678, dated Apr. 4, 2016, 11 pages.
Varga et al., "*Aspergillus calidoustus* sp. nov., causative agent of human infections previously assigned to Aspergillus ustus," Eukaryot Cell., 2008, 7: 630-638.
Walsh et al., "Treatment of aspergillosis: clinical practice guidelines of the Infectious Diseases Society of America," Clin Infect Dis., Feb. 1, 2008;46(3):327-60.
EP Office Action in European Appln. No. 15802361.4, dated Jul. 19, 2022, 8 pages.

\* cited by examiner

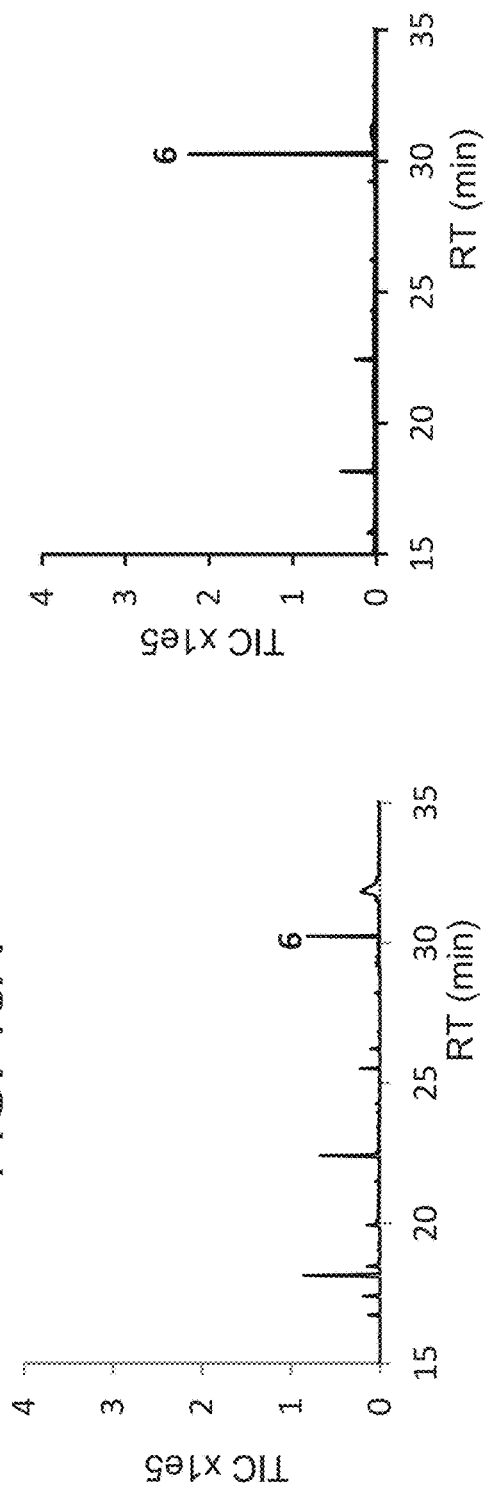
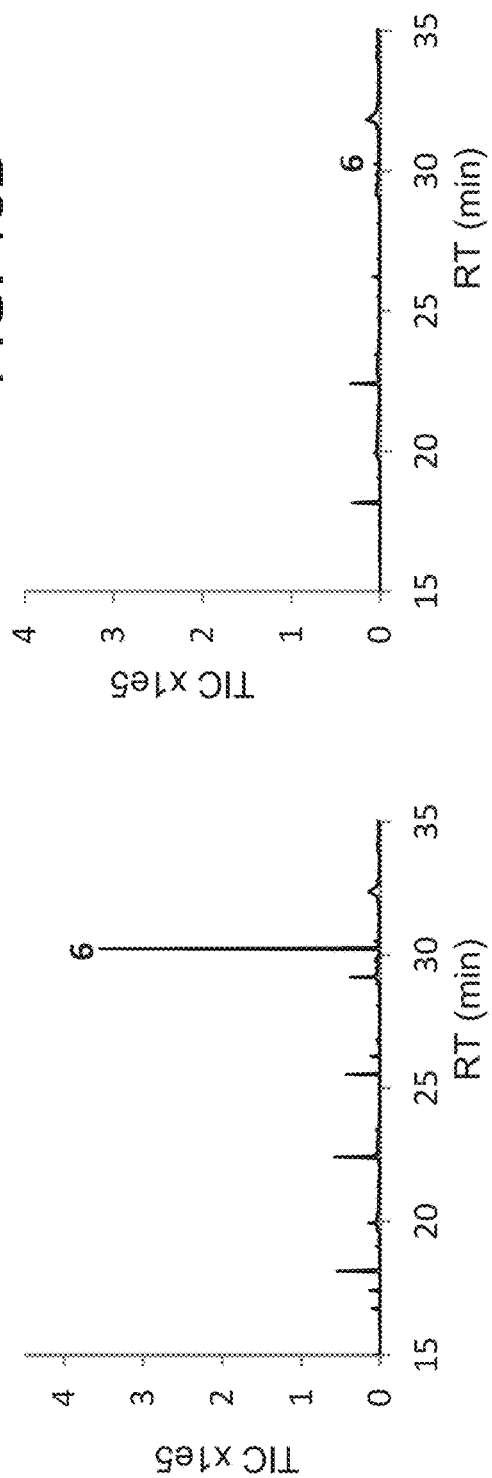

DIAGNOSIS AND TREATMENT OF INVASIVE ASPERGILLOSIS

CLAIM OF PRIORITY

This application is a continuation of U.S. patent application Ser. No. 16/298,521, filed Mar. 11, 2019, which is a continuation of U.S. patent application Ser. No. 15/316,062, filed Dec. 2, 2016, now U.S. Pat. No. 10,227,629, which is a § 371 National Stage Application of PCT/US2015/034182, filed Jun. 4, 2015, which claims the benefit of U.S. Provisional Patent Application Ser. Nos. 62/008,419, filed on Jun. 5, 2014, and 62/050,583, filed on Sep. 15, 2014. The entire contents of the foregoing are hereby incorporated by reference.

FEDERALLY SPONSORED RESEARCH OR DEVELOPMENT

This invention was made with Government support under Grants No. R21AI085454 and K23AI097225 awarded by the National Institutes of Health. The Government has certain rights in the invention.

TECHNICAL FIELD

Provided herein are methods for diagnosing, treating, and monitoring the treatment of invasive aspergillosis (IA). The methods can include detecting the presence of one or more volatile organic compounds (VOCs) in the breath of subjects suspected of having IA.

BACKGROUND

IA is a common, rapidly progressive, highly morbid, and frequently fatal infection in immunocompromised patients, especially in patients with chemotherapy-induced neutropenia or who are immunosuppressed as a result of receiving glucocorticoid treatment for graft-versus-host disease (GVHD). Timely diagnosis with prompt initiation of appropriate antifungal therapy improves clinical outcomes. Unfortunately, clinical and radiographic manifestations are nonspecific, and standard culture and antigen diagnostic approaches lack sensitivity and specificity for IA. Definitive diagnosis still relies on biopsy, which is often unacceptably morbid and frequently uninformative in these debilitated patients.

SUMMARY

As described herein, the present inventors have (1) identified a unique, species-specific profile of volatile organic compounds (VOCs) produced by *Aspergillus fumigatus, A. terreus, A. calidoustus*, and other pathogenic fungi in vitro that can be used to distinguish pathogenic fungal species from each other, (2) demonstrated that differential mobility spectrometry (DMS) can be used for the rapid discrimination between fungal species using pattern-based detection of these species-specific VOC profiles, and (3) accurately identified patients with invasive aspergillosis (IA) via direct detection of a pattern of *A. fumigatus* VOCs in their breath, including a combination of beta-trans-bergamotene, beta-vatirenene, and trans-geranylacetone.

Thus in a first aspect, the invention provides methods for diagnosing a subject with invasive aspergillosis (IA). The methods include obtaining a sample comprising breath of a subject or headspace from a culture suspected of comprising *Aspergillus* isolated from a subject; detecting the presence in the sample of one, two, three, or more volatile organic compounds (VOCs) produced by the *Aspergillus* species in a sample comprising breath from the subject or headspace from a culture suspected of comprising *Aspergillus* isolated from the subject, wherein the VOCs are selected from the group consisting of camphene, α-pinene, β-pinene, limonene, α-trans-bergamotene, β-trans-bergamotene, trans-geranylacetone, beta-trans-bergamotene, beta-vatirenene, trans-geranylacetone, camphene, alpha-pinene, beta-pinene, limonene, alpha-bergamotene, beta-trans-bergamotene, elixene, alpha-santalene, beta-elemene, acoradien, chamigrene, 1,5,9-trimethyl cyclododecatriene, 9-decene-2-one and beta-sesquiphellandrene; and diagnosing a subject as having IA based on the presence of (i.e., when there are) one, two, three or more of the VOCs in the sample.

In some embodiments, the methods include detecting the presence in the sample of one, two or three VOCs selected from the group consisting of camphene, α-pinene, β-pinene, limonene, α-trans-bergamotene, β-trans-bergamotene, trans-geranylacetone, beta-trans-bergamotene, beta-vatirenene and trans-geranylacetone; and diagnosing a subject who has one, two or all three of beta-trans-bergamotene, beta-vatirenene and trans-geranylacetone in the sample as having IA. In preferred embodiments, a diagnosis of IA is based on the presence of all three of the VOCs α-trans-bergamotene, β-trans-bergamotene, and trans-geranylacetone in the sample.

In another aspect, the invention provides methods for treating a subject who has invasive aspergillosis (IA). The methods include obtaining a sample comprising breath of a subject or headspace from a culture suspected of comprising *Aspergillus* isolated from a subject; detecting the presence in the sample of one, two or three VOCs selected from the group consisting of α-trans-bergamotene, β-trans-bergamotene, trans-geranylacetone, and administering an antifungal treatment to a subject who has one, two or all three of beta-trans-bergamotene, beta-vatirenene and trans-geranylacetone in their breath or camphene, α-pinene, β-pinene, limonene, α-trans-bergamotene, and β-trans-bergamotene in headspace from a culture.

In some embodiments, the treatment includes administration of one or more doses of one or more antifungal compounds, e.g., an amphotericin B formulation; an azole compound; and an echinocandin.

In another aspect, the invention provides methods for detecting the presence of an *Aspergillus fumigatus, A. terreus*, or *A. calidoustus* infection in a subject. The methods include obtaining a sample comprising breath of a subject, or headspace from a culture suspected of comprising *Aspergillus* isolated from a subject; determining the presence of one, two, three, or more, e.g., all, of the VOCs selected from the group consisting of camphene, alpha-pinene, beta-pinene, limonene, α-trans-bergamotene, β-trans-bergamotene, trans-geranylacetone, elixene, alpha-santalene, beta-elemene, acoradien, chamigrene, 1,5,9-trimethyl cyclododecatriene, 9-decene-2-one and beta-sesquiphellandrene in the sample. The presence of one, two, three, or more, e.g., all, of camphene, α-pinene, β-pinene, limonene, α-trans-bergamotene, β-trans-bergamotene in headspace, or α-trans-bergamotene, β-trans-bergamotene, and trans-geranylacetone in breath, indicates the presence of an *A. fumigatus* infection; the presence of one, two, three, or more, e.g., all, of elixene, alpha-santalene, beta-elemene, acoradien, chamigrene, and 1,5,9-trimethyl cyclododecatriene indicates the presence of an *A. terreus* infection; and the presence of one or both of 9-decene-2-one and beta-sesquiphellandrene indicates the presence of an *A. calidoustus* infection in the subject.

In some embodiments, the methods include selecting, and optionally administering, a therapy comprising an azole, e.g., voriconazole, for a subject who has an *A. fumigatus* or *A. terreus* infection; or selecting, and optionally administering, a therapy comprising amphotericin B (AMB), e.g., D-AMB or a lipid formulation of AMB, for a subject who has an *A. calidoustus* infection.

In another aspect, the invention provides methods for monitoring efficacy of a treatment for invasive aspergillosis (IA) in a subject. The methods include determining a first level of one, two, three, or more volatile organic compounds (VOCs) produced by the *Aspergillus* species in a sample comprising breath from the subject or headspace from a culture suspected of comprising *Aspergillus* isolated from the subject, wherein the VOCs are selected from the group consisting of camphene, alpha-pinene, beta-pinene, limonene, α-trans-bergamotene, β-trans-bergamotene, trans-geranylacetone, elixene, alpha-santalene, beta-elemene, acoradien, chamigrene, 1,5,9-trimethyl cyclododecatriene, 9-decene-2-one and beta-sesquiphellandrene, in the subject; administering a treatment for IA to the subject; determining a second level of the VOCs in a sample obtained after administration of the treatment to the subject; and comparing the first and second levels of VOCs. A decrease in the VOCs indicates that the treatment has been effective in treating the IA in the subject, and an increase or no change indicates that the treatment has not been effective in treating the IA in the subject.

In some embodiments, the treatment includes administration of one or more doses of one or more antifungal compounds, e.g., an amphotericin B formulation; an azole compound; and an echinocandin.

In yet another aspect, the invention provides methods for identifying a candidate compound for the treatment of IA. The methods include providing a test culture comprising one or more *Aspergillus* species; detecting a baseline level of fungal VOCs in the headspace of the culture in the absence of the test compound, wherein the VOCs are selected from the group consisting of camphene, alpha-pinene, beta-pinene, limonene, α-trans-bergamotene, β-trans-bergamotene, trans-geranylacetone, elixene, alpha-santalene, beta-elemene, acoradien, chamigrene, 1,5,9-trimethyl cyclododecatriene, 9-decene-2-one and beta-sesquiphellandrene, in the subject; contacting the test culture with a test compound; determining a second level of the VOCs in a the test culture; comparing the second level of VOCs to the baseline level; and identifying a test compound that decreases levels of fungal VOCs in the test culture as a candidate compound for the treatment of IA.

In another aspect, the invention provides methods for detecting the presence of an *Aspergillus fumigatus*, *A. terreus*, or *A. calidoustus* infection in a culture. The methods include obtaining a sample from the culture, e.g., gas from the headspace of the culture; determining the presence of one, two, three, or more, e.g., all, of the VOCs selected from the group consisting of camphene, alpha-pinene, beta-pinene, limonene, α-trans-bergamotene, β-trans-bergamotene, trans-geranylacetone, elixene, alpha-santalene, beta-elemene, acoradien, chamigrene, 1,5,9-trimethyl cyclododecatriene, 9-decene-2-one and beta-sesquiphellandrene in the sample. The presence of one, two, three, or more, e.g., all, of camphene, alpha-pinene, beta-pinene, limonene, α-trans-bergamotene, β-trans-bergamotene, and/or trans-geranylacetone, indicates the presence of *A. fumigatus* in the culture; the presence of one, two, three, or more, e.g., all, of elixene, alpha-santalene, beta-elemene, acoradien, chamigrene, and 1,5,9-trimethyl cyclododecatriene indicates the presence of *A. terreus* in the culture; and the presence of one or both of 9-decene-2-one and beta-sesquiphellandrene indicates the presence of *A. calidoustus* infection in the culture.

In some embodiments of the various methods described herein, determining the presence of a VOC comprises assaying the sample to detect the presence the VOC. In some embodiments, assaying the sample to detect the presence the VOC comprises using a gas chromatography (GC) or spectrometry method. In some embodiments, the spectrophotometry method is mobility spectrometry (IMS) or differential mobility spectrometry (DMS).

In some embodiments of the various methods described herein, the subject is a human.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety, including especially U.S. Application Ser. No. 61/698,155, filed on Sep. 7, 2012, and PCT/US2013/058560, filed on Sep. 6, 2013, and published as WO 2014/039856. In case of conflict, the present specification, including definitions, will control.

Other features and advantages of the invention will be apparent from the following detailed description and figures, and from the claims.

DESCRIPTION OF DRAWINGS

FIGS. 18A-D. Effect of antifungal drug exposure on the volatile organic compound profile of *A. fumigatus* Af293 GC-MS analysis of *A. fumigatus* Af293 after 12 hours of exposure to (A) no antifungal therapy; (B) liposomal amphotericin; (C) micafungin; or (D) voriconazole. Peak 6 identified as β-trans-bergamotene. TIC, total ion count; RT, retention time.

DETAILED DESCRIPTION

Figure 1:
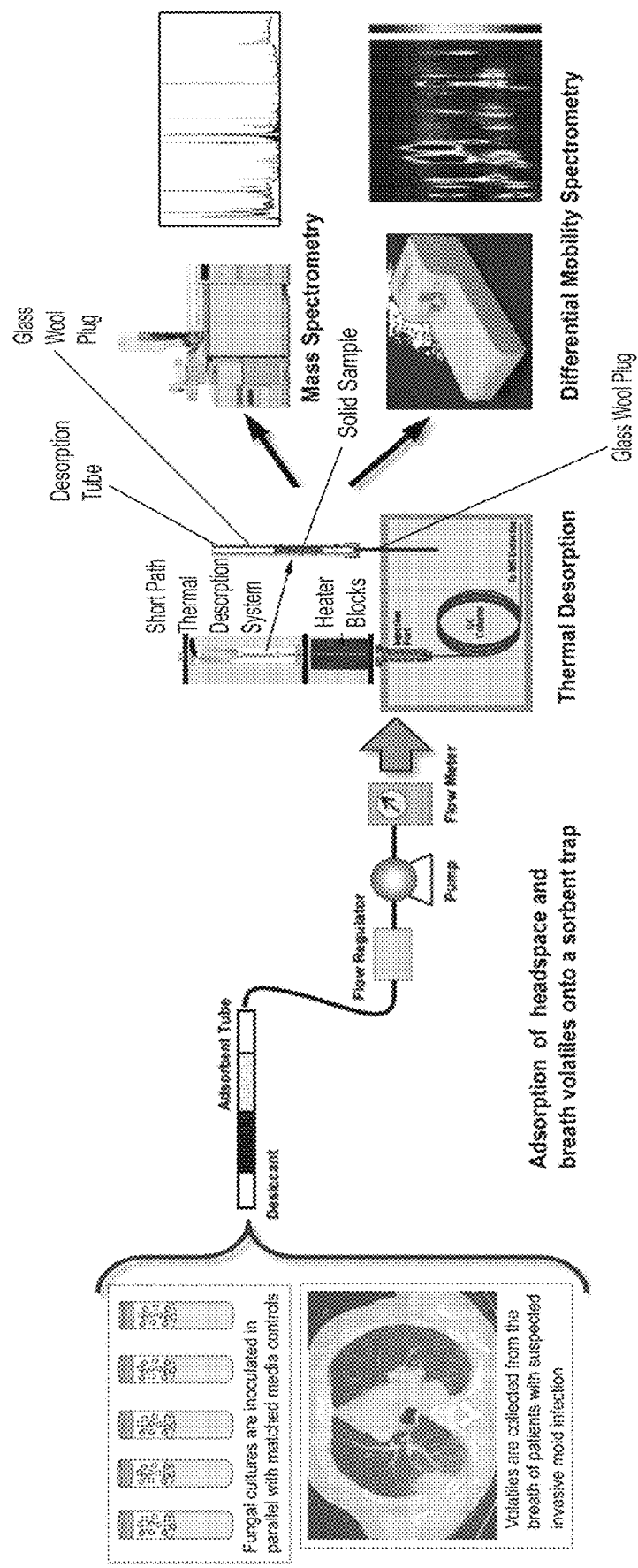
FIG. 1. Collection of VOCs from headspace gas of in vitro cultures or patient breath, with concentration of VOCs on a thermal desorption trap, thermal desorption onto the GC, and parallel data acquisition on a dual mass spectrometry/differential mobility spectrometry system.

Pathogenic molds produce VOCs as part of their normal metabolism. Agricultural and environmental health industries have previously investigated the detection of microbial VOCs to identify spoiled grain and mold-infested 'sick buildings,' respectively, and investigators in these areas have noticed species-specific differences in the composition of VOCs emitted by molds in these settings.

As described herein, the present inventors have identified unique, species-specific VOC profiles of *A. fumigatus*, *A. terreus*, and *A. calidoustus* in vitro, including several volatile terpene and sesquiterpene compounds that can be used to discriminate these species from each other and from other molds, and demonstrated that differential mobility spectrometry (DMS) can be used for the rapid discrimination of fungal species using pattern-based identification of these species-specific VOC profiles. The key terpene and sesquiterpene compounds identified in in vitro cultures of *A. fumigatus* were also present in the breath of patients with IA, in addition to novel *Aspergillus* VOCs induced in vivo, namely, the sesquiterpene beta-vatirenene and the oxidized terpene derivative trans-geranylacetone. A combination of beta-trans-bergamotene, beta-vatirenene, and trans-geranylacetone accurately distinguished patients with IA from patients with other causes of pneumonia with 93% sensitivity and 96% specificity.

Detection of these unique VOC profiles can be harnessed for species-level identification of *Aspergillus* and other mold species in the laboratory, and direct detection of these fungal volatile profiles in the breath of patients with suspected IA can be used for the rapid, noninvasive, highly accurate, and species-specific diagnosis of IA and other fungal pneumonias. The methods and devices described herein, e.g., the DMS-based detection methods, can be adapted to a small, portable bedside breath gas detection system for real-time patient breath surveillance for this pattern of fungal metabolites, to allow for earlier IA diagnosis than currently possible, more rational test-based prescribing of antifungal medications, monitoring of clinical response to antifungal therapy, and ultimately, better patient outcomes.

As described herein, among other uses, these VOC profiles can be used for:

a. rapid, noninvasive, sensitive, and species-specific breath tests for the diagnosis of invasive aspergillosis and the discrimination of aspergillosis from other causes of pneumonia in the growing population of immunocompromised patients at risk for invasive fungal infections;

b. surrogate marker demonstrating successful antifungal treatment of IA, and c. rapid identification and antifungal susceptibility testing of *Aspergillus* species, e.g., in the microbiology laboratory, based on their VOC profile (i.e., the VOCs present in the sample).

Invasive Aspergillosis

The methods described herein can be used to detect or diagnose invasive aspergillosis (IA) in a subject, to select treatment and to treat IA, and to monitor treatment of IA. The methods can be used in the different forms of invasive aspergillosis, including invasive pulmonary aspergillosis, sinus or nasal aspergillosis, disseminated aspergillosis, and single-organ invasive aspergillosis, e.g., of an organ in the sino/nasal/respiratory tract (see, e.g., Walsh et al., Clinical Infectious Diseases 2008; 46:327-60; Milroy et al., J Clin Pathol. 1989 February; 42(2): 123-127). In preferred embodiments, the methods described herein can be used for subjects with invasive pulmonary aspergillosis.

Samples

The methods described herein can be performed on a gas or liquid sample. In some embodiments, the sample is exhaled breath directly from an individual or from a breathing machine such as a ventilator. Alternatively, the methods can be performed using headspace from a culture known or suspected to include *Aspergillus* species, e.g., commercially-available or lab-cultured species or species obtained from a primary sample from a subject, e.g., a clinical sample obtained by biopsy of the affected area (e.g., nasal biopsy, transthoracic percutaneous needle aspiration, or video assisted thoracoscopic biopsy) or bronchoalveolar lavage. The sample is maintained in a suitable growth medium to allow growth and metabolism of any *Aspergillus* species in the sample. In certain embodiments, the invention involves taking a clinical sample from a subject and placing it in media, for example, with microfluidics, or in culture, for example, with conventional culturing methods. The *Aspergillus* species, if present, are stimulated to metabolize. The headspace (gaseous phase) generated as a result of this metabolism can be collected and analyzed using a method described herein or known in the art, see, e.g., US20100291617. In some embodiments, the methods are performed directly on bronchoalveolar washings, obtained by bronchoscopy/bronchoalveolar lavage. In some embodiments, the sample is a gas, e.g., patient breath or gas from the headspace of an in vitro culture sample. Where headspace gas is used, the gas should be collected after the headspace has been in contact with the culture for a sufficient amount of time for the compounds to be present, preferably in an air-tight, sealed environment.

The VOCs can also be detected in a liquid sample, since they are expected to be there in equilibrium with the gaseous phase. Thus, in addition to or as an alternative, the samples assayed using the methods described herein can include a liquid, e.g., blood (e.g., plasma or serum), lymph, urine, tears, saliva, sputum, nasal mucus, phlegm (e.g., expectorate), or CSF from a subject (e.g., from a biological fluid that comes near or preferably into contact with the tissue or organ that is known or suspected to be infected with an *Aspergillus* species), or the liquid phase (e.g., supernatant) of an in vitro culture. In some embodiments, the sample comprises saliva from the subject.

Detection Methods

A number of methods known in the art can be used to detect the presence of the VOCs described herein in a sample. Exemplary methods (particularly for use with a gas sample) include gas chromatography (GC); spectrometry, for example mass spectrometry (including quadrapole, time of flight, tandem mass spectrometry, ion cyclotron resonance, and/or sector (magnetic and/or electrostatic)), ion mobility spectrometry, field asymmetric ion mobility spectrometry, and/or DMS; fuel cell electrodes; light absorption spectroscopy; nanoparticle technology; flexural plate wave (FPW) sensors; electrochemical sensors; photoacoustic equipment; laser-based equipment; electronic noses (bio-derived, surface coated); and various ionization techniques. See, e.g., US20100291617 and US20070003996. Preferred methods include ion mobility spectrometry (IMS) or differential mobility spectrometry (DMS).

In some embodiments, the methods described herein include the use of differential mobility spectrometry to detect VOCs in a sample. An exemplary micro-machined differential mobility spectrometer (DMS), developed for chemical and biological sensing applications, is currently available from Sionex Corporation. DMS has several features that make it an excellent platform for VOC analysis: it is quantitative, selective, and exquisitely sensitive, with a volatile detection limit in the parts-per-trillion range (Davis et al., In: 12th International Conference on Transducers, Solid-State Sensors, Actuators and Microsystems; 2003; p. 1233-8 vol. 2; Miller et al., In: Solid-State Sensors and Actuators Workshop; 2000; Hilton Head, S.C.; 2000; Krebs et al., Sensors Journal, IEEE 2005; 5(4):696-703). Unlike mass spectrometry, which separates particles based on mass/charge ratios, DMS harnesses differences in ion mobility in low and high electric fields to achieve a gas-phase separation of ions at atmospheric pressure. DMS rapidly detects compounds that are difficult to resolve by other analytical techniques such as mass spectrometry in challenging matrices such as human breath (Kanu et al., J Mass Spectrom 2008; 43:1-22; Kanu et al., J Chromatogr A 2008; 1177:12-27; Luong J et al., J Chromatogr Sci 2006; 44:276-286; Nazarov et al., Anal Chem 2006; 7697-706; Kolakowski et al., Analyst 2007; 132:842-64).

DMS can be tuned to monitor specific ion masses, thus tailoring response characteristics to focus on various compounds of interest. It requires no reagents, generates the high fields required by the sensor using a small power supply, and has already been microfabricated, resulting in a small, portable machine that can be used at the bedside, with a turnaround time of several minutes. DMS has been used successfully in several commercial settings, including a hand-held, portable detector of trace levels of chemical warfare agents from General Dynamics (JUNO™) and airport explosives detectors from Thermo (see, e.g., U.S. Pat. No. 7,605,367). DMS technology has also been successfully applied to the characterization of unique VOCs produced by *Mycobacterium tuberculosis* and other bacteria (Fong et al., Anal Chem 2011; 83:1537-46; Shnayderman et al., Anal Chem 2005; 77:5930-7).

To perform a measurement using a DMS, a gas sample is introduced into the spectrometer, where it is ionized, and the ions are transported through an ion filter towards the detecting electrodes (Faraday plates) by a carrier gas. The DMS device can separate chemical components of a substance based on differing ion mobilities. For other devices, measurements are performed using methods known in the art.

Additional non-limiting examples of systems that can be used in the present methods include those described in US20090078865; US20130168548; US20100291617 and US20070003996.

In some embodiments, the methods include obtaining a sample of ambient air and detecting the presence and/or levels of VOCs in the air, to provide a reference for subtraction of ambient VOCs.

A number of methods are known in the art for detecting the presence and/or levels of the VOCs in a liquid sample, including but not limited to chromatography (e.g., HPLC) and spectrophotometry (e.g., MS, LC-MS, MALDI-TOF, and other of the methods described above for gas-phase samples).

Combination Diagnostics

In some embodiments, the methods include performing an additional diagnostic test for IA. A number of such tests are known in the art and include galactomannan enzyme immunoassays; radiology imaging studies (e.g., CT imaging); bronchoalveolar lavage, transthoracic percutaneous needle aspiration, or video assisted thoracoscopic biopsy. A positive result on one of these tests can provide further evidence supporting a diagnosis of IA; see, e.g., Walsh et al., Clinical Infectious Diseases 2008; 46:327-60.

*Aspergillus* Species Identification and Diagnosis

As described herein, *A. fumigatus*, *A. terreus*, *A. calidoustus* each produce VOCs that can be used to identify them in a sample, e.g., in a sample comprising breath of a subject, or headspace from a culture suspected of comprising *Aspergillus*; the culture can be, e.g., a culture of a biopsy from a subject, or a culture in a microbiology laboratory, e.g., a culture known or suspected of containing or being contaminated with an *Aspergillus* species. This identification can be used to diagnose a subject with the specific species of *Aspergillus*, allowing for the administration of species-specific treatments, e.g., as described below.

Thus, the methods described herein can include obtaining a sample comprising breath of a subject, or headspace from a culture suspected of comprising *Aspergillus*, and detecting and identifying the VOCs in the sample. For example, the methods can include detecting the presence of one, two, three, or more, e.g., all, of camphene, alpha-pinene, beta-pinene, limonene, alpha-bergamotene, beta-trans-bergamotene, elixene, alpha-santalene, beta-elemene, acoradien, chamigrene, 1,5,9-trimethyl cyclododecatriene, 9-decene-2-one and beta-sesquiphellandrene in the sample. The presence of one, two, three, or more, e.g., all, of camphene, alpha-pinene, beta-pinene, limonene, alpha-bergamotene, or beta-trans-bergamotene indicates the presence of *A. fumigatus* in the sample (and thus an *A. fumigatus* infection in cases where the sample is from a subject); the presence of one, two, three, or more, e.g., all, of elixene, alpha-santalene, beta-elemene, acoradien, chamigrene, and 1,5,9-trimethyl cyclododecatriene indicates the presence of *A. terreus* in the sample (and thus an *A. terreus* infection in cases where the sample is from a subject); and the presence of one or both of 9-decene-2-one and beta-sesquiphellandrene indicates the presence of *A. calidoustus* in the sample (and thus an *A. calidoustus* infection in cases where the sample is from a subject). In some embodiments, where limonene or alpha-pinene is present, at least one or two other VOCs must also be present for a positive species identification, and a species-specific diagnosis, to be made.

Methods of Treatment

The methods described herein can be used to select a treatment for a subject, and can optionally include administering the treatment to a subject. When a subject has been diagnosed by a method described herein as having IA, then a treatment comprising administration of a therapeutically effective amount of an antifungal compound can be administered.

A number of antifungal compounds are known in the art and under development. At present, deoxycholate amphotericin B (D-AMB) and its lipid formulations (AMB lipid complex (ABLC), liposomal amphotericin B (LAMB), and Amphotericin B cholesteryl sulfate complex (AMB colloidal dispersion, ABCD)); azole compounds (itraconazole, voriconazole, posaconazole); and echinocandins (caspofungin, micafungin, anidulafungin) are in clinical use, though voriconazole and D-AMB are the only compounds approved for primary treatment of invasive aspergillosis in the United States. For detailed information on treatment of IA, see, e.g., Walsh et al., Clinical Infectious Diseases 2008; 46:327-60; and Marr et al., *Treatment and prevention of invasive aspergillosis*, Up-To-Date (topic updated on Oct. 18, 2012; literature review August 2013; available at uptodate.com/contents/treatment-and-prevention-of-invasive-aspergillosis?topicKey=ID%2F2459&elapsedTimeMs=7&view=print&displayedView=full).

In some embodiments, the methods include selecting and optionally administering an azole antifungal, e.g., itraconazole (ITR), voriconazole (VOR), posaconazole (POS), ravuconazole (RAV), or isavuconazole (ISA), or an amphotericin B (AMB) formulation as described above, to a subject identified by a method described herein as having IA. In some embodiments, the methods include administering an echinocandin, e.g., caspofungin, micafungin or anidulafungin, e.g., alone or in combination with an azole (e.g., voriconazole) or AMB.

It is known that triazoles are not active against some isolates of *A. calidoustus*, and some *A. terreus* isolates are resistant to AMB. See, e.g., Baddley et al., J. Clin. Microbiol. 2009, 47(10):3271. Thus, in some embodiments, where the species of *Aspergillus* is determined, an azole compound (e.g., ITR, VOR, POS, RAV, or ISA) is selected for (and optionally administered to) a subject who has *A. fumigatus* or *A. terreus*, but not *A. calidoustus*. In some embodiments, an AMB (e.g., D-AMB, ABLC, LAMB, or ABCD) is selected for (and optionally administered to) a subject who has *A. calidoustus*. In some embodiments, an AMB is selected for (and optionally administered to) a subject who has *A. fumigatus*, but not a subject who has *A. terreus*.

In some embodiments, the methods described herein can be used to determine susceptibility of *Aspergillus* species, e.g., to treatment with a known or suspected antifungal, e.g., in the microbiology laboratory. A sample suspected or known to include *Aspergillus* from a subject is obtained and cultured as described above, e.g., under conditions mimicking the in vivo environment, and then exposed to a potential treatment (e.g., a known or experimental treatment). After exposure to the treatment, the VOCs present in the headspace of the culture are sampled. If the treatment decreases VOCs as compared to a reference level (e.g., a level of VOCs in the headspace before exposure to the treatment), then the *Aspergillus* in the sample is considered susceptible to the treatment. In this case, the treatment is likely to be effective in treating IA in the subject; the treatment can be selected and optionally administered to subject.

Monitoring Treatment Efficacy

As described herein, successful treatment of an *Aspergillus* infection results in a decrease in fungal VOCs. Thus, the methods can include repeated assays of VOC levels in a subject, e.g., before, during, and after administration of a treatment for IA. A decrease in VOC levels would indicate that the treatment has been successful. In some embodiments, levels of one, two, or all three of beta-trans-bergamotene, beta-vatirenene, and/or trans-geranylacetone are determined. In some embodiments, levels of one, two, three, or more of beta-trans-bergamotene, beta-vatirenene, trans-geranylacetone, camphene, alpha-pinene, beta-pinene, limonene, alpha-bergamotene, beta-trans-bergamotene, elixene, alpha-santalene, beta-elemene, acoradien, chamigrene, 1,5,9-trimethyl cyclododecatriene, 9-decene-2-one and beta-sesquiphellandrene are determined.

Methods of Identifying Novel Antifungal Agents

Included herein are methods for screening test compounds, e.g., polypeptides, polynucleotides, inorganic or organic large or small molecule test compounds, to identify agents useful in the treatment of IA.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, *Solid-Supported Combinatorial and Parallel Synthesis of Small-Molecular-Weight Compound Libraries*, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids.

In some embodiments, the test compounds and libraries thereof can be obtained by systematically altering the structure of a first test compound, e.g., a first test compound that is structurally similar to a known natural binding partner of the target polypeptide, or a first small molecule identified as capable of binding the target polypeptide, e.g., using methods known in the art or the methods described herein, and correlating that structure to a resulting biological activity, e.g., a structure-activity relationship study. As one of skill in the art will appreciate, there are a variety of standard methods for creating such a structure-activity relationship. Thus, in some instances, the work may be largely empirical, and in others, the three-dimensional structure of an endogenous polypeptide or portion thereof can be used as a starting point for the rational design of a small molecule compound or compounds. For example, in one embodiment, a general library of small molecules is screened, e.g., using the methods described herein.

In some embodiments, a test compound is applied to a test sample comprising one or more *Aspergillus* species, and the ability of the test compound to decrease levels of a VOC as described herein in the headspace of the culture is determined.

In some embodiments, the test sample is, or is derived from (e.g., a sample taken from) an in vivo model of a disorder as described herein. For example, an animal model, e.g., a rodent (such as a rat or mouse) that has been infected with one or more *Aspergillus* species can be used.

A test compound that has been screened by a method described herein and determined to decrease VOCs, can be considered a candidate compound. A candidate compound that has been screened, e.g., in an in vivo model of a disorder, e.g., a rodent infected with one or more *Aspergillus* species, and determined to decrease VOCs in a sample comprising breath from the infected animal model or headspace from a culture of a sample from the infected animal model, can be considered a candidate therapeutic agent. Candidate therapeutic agents, once screened in a clinical setting, are therapeutic agents. Candidate compounds, candidate therapeutic agents, and therapeutic agents can be optionally optimized and/or derivatized, and formulated with physiologically acceptable excipients to form pharmaceutical compositions.

Thus, test compounds identified as "hits" (e.g., test compounds that decrease fungal VOCs in an animal model) in a first screen can be selected and systematically altered, e.g., using rational design, to optimize binding affinity, avidity, specificity, or other parameter. Such optimization can also be screened for using the methods described herein. Thus, in one embodiment, the invention includes screening a first library of compounds using a method known in the art and/or described herein, identifying one or more hits in that library, subjecting those hits to systematic structural alteration to create a second library of compounds structurally related to the hit, and screening the second library using the methods described herein.

Test compounds identified as hits can be considered candidate therapeutic compounds, useful in treating IA. A variety of techniques useful for determining the structures of "hits" can be used in the methods described herein, e.g., NMR, mass spectrometry, gas chromatography equipped with electron capture detectors, fluorescence and absorption spectroscopy. Thus, the invention also includes compounds identified as "hits" by the methods described herein, and methods for their administration and use in the treatment, prevention, or delay of development or progression of a disorder described herein.

Test compounds identified as candidate therapeutic compounds can be further screened by administration to an animal model of IA, as described herein. The animal can be monitored for a change in the disorder, e.g., for an improvement in a parameter of the disorder, e.g., a parameter related to clinical outcome. In some embodiments, the parameter is VOCs or survival, and an improvement would be a reduction in VOCs or an increase in survival. In some embodiments, the subject is a human, e.g., a human with IA and the parameter is levels of fungal VOCs or survival.

EXAMPLES

The invention is further described in the following examples, which do not limit the scope of the invention described in the claims.

Example 1. Definition of *Aspergillus* VOC Profiles In Vitro

Using gas chromatography interfaced to mass spectrometry and differential mobility spectrometry (GC-MS/DMS), VOC profiles were characterized in the headspace gas of in vitro cultures of *Aspergillus* species pathogenic to humans, most notably *A. fumigatus, A. terreus*, and *A. calidoustus*, under incubation conditions designed to mimic the milieu of the human lung and promote hyphal growth (as *Aspergillus* spreads through hyphal growth and invasion of human tissue blood vessels and tissues in vivo).

Mold strains (Table A) were incubated at 25° C. on Sabouraud dextrose agar slants. Conidia were harvested and conidial suspensions were prepared in sterile water. Conidia were quantified with a hemocytometer.

TABLE A

Fungal species used for in vitro VOC profile determination

| Genus | Species | Strains (N) | Source* |
|---|---|---|---|
| Aspergillus | fumigatus | 9 | ATCC, CDC, BWH |
| Aspergillus | terreus | 7 | ATCC, BWH |
| Aspergillus | calidoustus | 3 | ATCC |
| Aspergillus | niger | 6 | CDC, BWH |
| Aspergillus | tubingensis | 2 | CDC |
| Aspergillus | flavus | 5 | CDC, BWH |
| Rhizopus | oryzae | 3 | ATCC, BWH |
| Fusarium | solani | 2 | ATCC, BWH |
| Mucor | velutinosus | 1 | BWH |

*ATCC: American Type Culture Collection, CDC: Centers for Disease Control; BWH: Brigham and Women's Hospital For each experiment, $10^4$ conidia were inoculated into 5 mL of microbial media (either nutrient Yeast Extract Peptone Dextrose (YPD) broth, nutrient poor *Aspergillus* minimal media (Pontecorvo et al., Advan Genet 1953; 5:141-238), or under iron-starved, alkaline stress, or nitrogen-depleted conditions (McDonagh et al., PLoS Pathog 2008; 4:e1000154)) in 20 mL glass vials with an airtight crimp top incorporating a rubber septum. Cultures were incubated for 24-144 hours at 200 rpm and 37° C. and headspace gas was dynamically adsorbed, using argon carrier gas and an air sampling pump calibrated to 20 mL/minute, onto Markes thermal desorption traps containing tandem beds of Tenax TA (200 mg), Carbograph 1 TD (100 mg), and Carboxen 1003 (100 mg), optimized to retain VOCs of diverse size and polarity.

Headspace VOCs were also collected after exposure of a subset of fungal isolates to the antifungal drugs voriconazole, liposomal amphotericin B, and micafungin, each at a concentration of 1.0 mg/mL.

VOCs were desorbed onto a dual GC-MS/DMS system (FIG. 1)—the eluent from the gas chromatograph was split between the MS, to allow identification of each compound, and the DMS, an extremely sensitive and selective gas detector that can be easily used as a point-of-care gas detection device, to determine the mobility pattern for each compound. The NIST MS Search 2.0 Library was used to identify VOCs in the total ion chromatogram (TIC) of the GC-MS data. Differences in spectral features of DMS output were visually distinguished between the positive ion spectra of *A. fumigatus* and *A. terreus* and principal component analysis (PCA) was used to evaluate the degree of class discrimination between these fungal species using algorithms in MATLAB (Version R2012a).

Collection of VOCs in Patient Breath

Breath was collected from patients with suspected IA using a Loccioni Breath Analysis sampler. For each patient, up to 4 minutes of tidal breath was adsorbed using an air sampling pump calibrated to 900 mL/minute onto two parallel thermal desorption traps containing tandem beds of Tenax TA (200 mg), Carbograph 1 TD (100 mg), and Carboxen 1003 (100 mg). Ambient air was sampled concurrently with each breath sample at a flow rate of 900 mL per minute to control for any environmental VOCs in patient breath samples. These samples were analyzed using the same thermal desorption GC-MS method outlined above for the in vitro fungal cultures.

Results

Figure 2A:
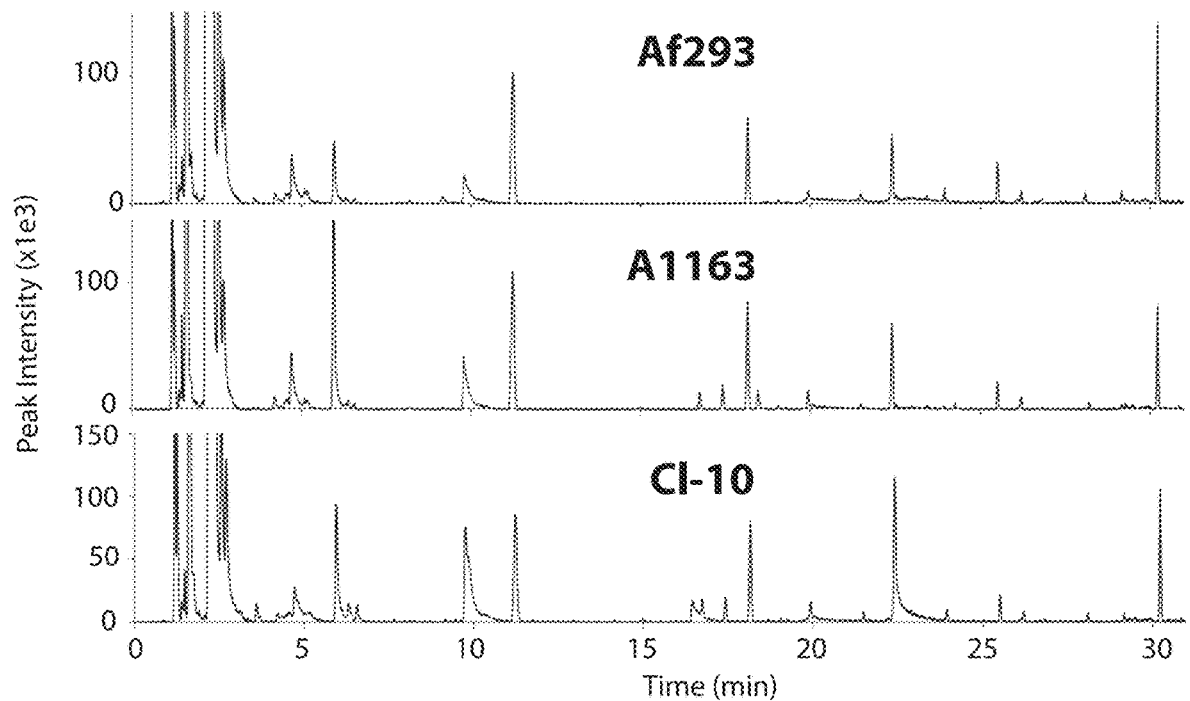
FIGS. 2A-B. A) Total ion chromatograms (TIC) generated by GC-MS of reference and clinical strains of *A. fumigatus* at 96 hrs in YPD media, showing the reproducibility of the VOC profile within species. B) GC-MS TIC of common pathogenic fungal species, showing interspecies VOC profile heterogeneity.
Figure 2B:
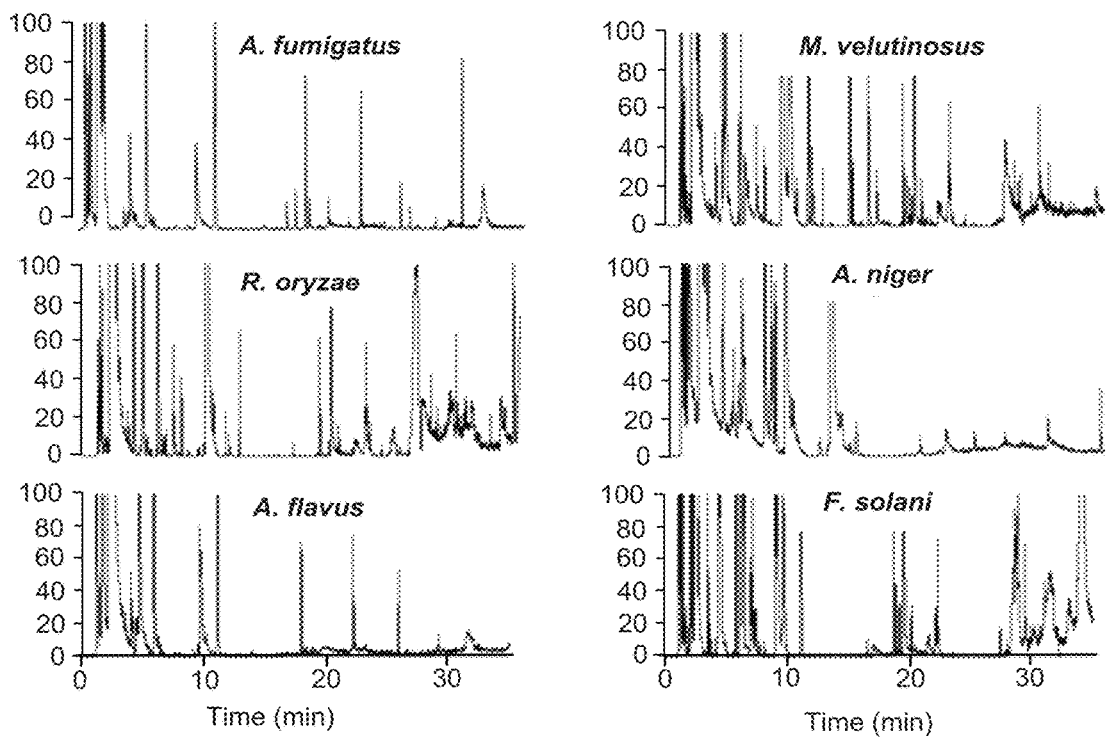

Intraspecies Homogeneity, Interspecies Heterogeneity of VOC Profiles:

Each mold species tested in vitro produced a distinctive VOC profile that was conserved within each species (FIG. 2A) and distinct between species (FIG. 2B). Terpene and sesquiterpene compounds were particularly distinct between different fungal species.

Figure 3:
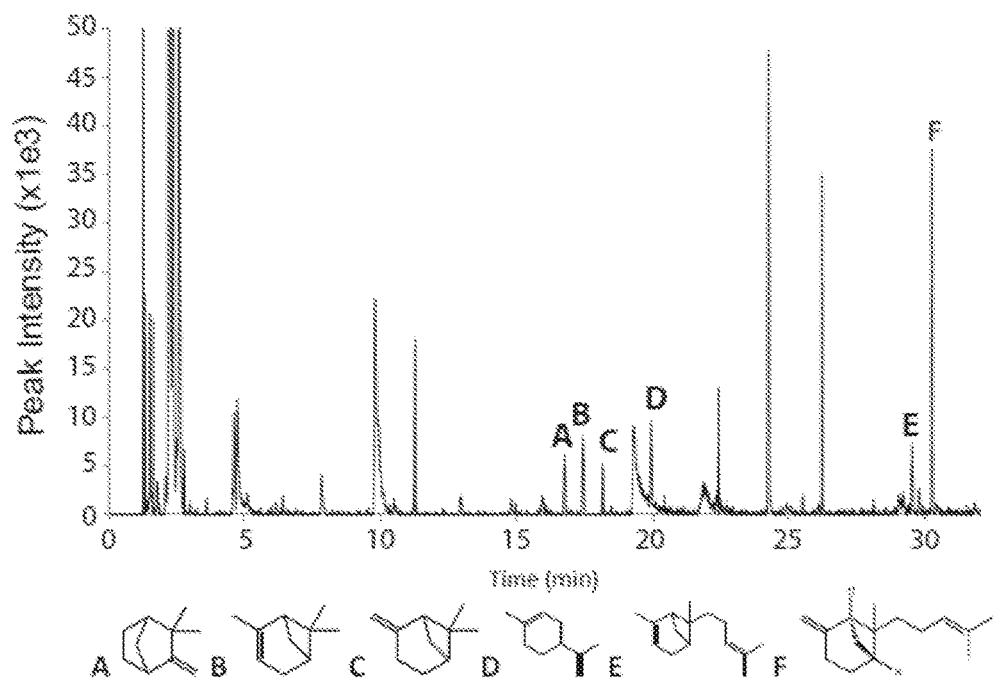
FIG. 3. Key features of the *A. fumigatus* VOC profile: A. camphene, B. α-pinene, C. β-pinene, D. limonene, E. α-bergamotene, and F. beta-trans-bergamotene.
Figure 4:
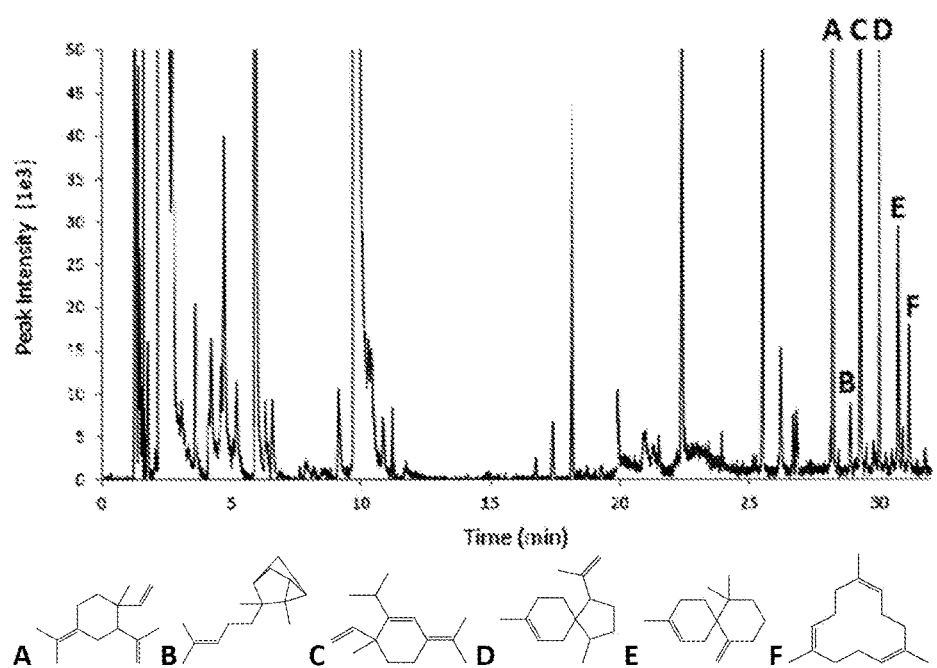
FIG. 4. Key features of the *A. terreus* VOC profile: A. elixene, B. α-santalene, C. β-elemene, D. acoradien, E. chamigrene, and F. 1,5,9-trimethyl cyclododecatriene.
Figure 5:
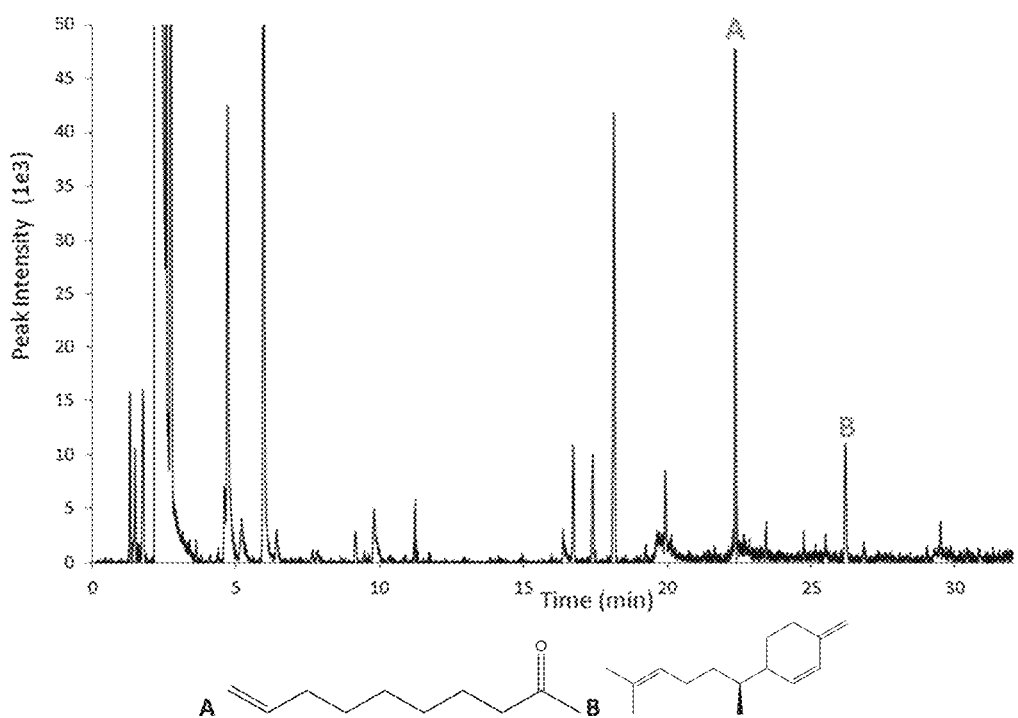
FIG. 5. Key features of the *A. calidoustus* VOC profile: A. 9-decene-2-one, B. β-sesquiphellandrene.

Comparison of the VOC profile of *A. fumigatus* with other fungal species showed that camphene, alpha-pinene, beta-pinene, limonene, alpha-bergamotene, and beta-trans-bergamotene were characteristic of *A. fumigatus* (FIG. 3). Comparison of the VOC profile of *A. terreus* with other fungal species showed that elixene, alpha-santalene, beta-elemene, acoradien, chamigrene, and 1,5,9-trimethyl cyclododecatriene were key features characteristic of *A. terreus* (FIG. 4). Comparison of the VOC profile of *A. calidoustus* with other fungal species showed that 9-decene-2-one and beta-sesquiphellandrene were key VOC features characteristic of *A. calidoustus* (FIG. 5).

Figure 6:
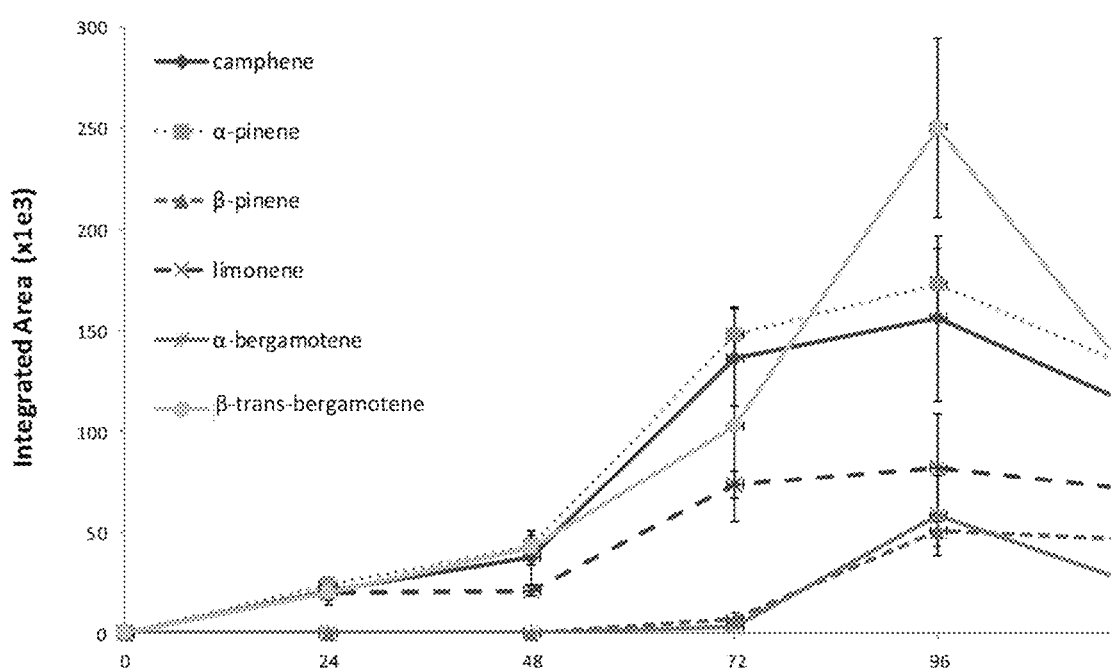
FIG. 6. Kinetics of *A. fumigatus* VOC emission with hyphal growth.

Kinetics of VOC Production In Vitro:

The kinetics of VOC release were assessed in vitro over lag, log, stationary, and death phases of each mold species, over 24-144 hours of incubation at 37° C. The key VOC features of *A. fumigatus* were first clearly discernible at 24 hours of incubation and all volatiles reached their peak concentration at 96 hours of incubation (FIG. 6).

Figure 7:
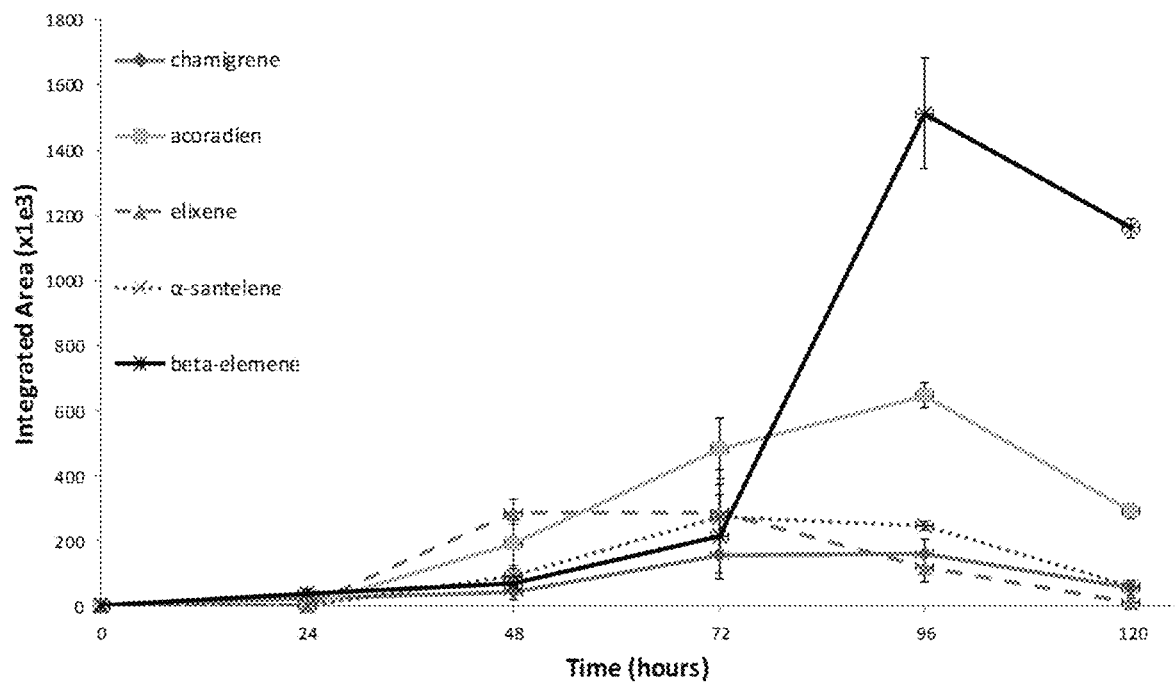
FIG. 7. Kinetics of *A. terreus* VOC emission with hyphal growth.

The key VOC features of *A. terreus* were first clearly discernible at 48 hours of incubation and reached peak levels at 96-120 hours of incubation (FIG. 7).

Figure 8:
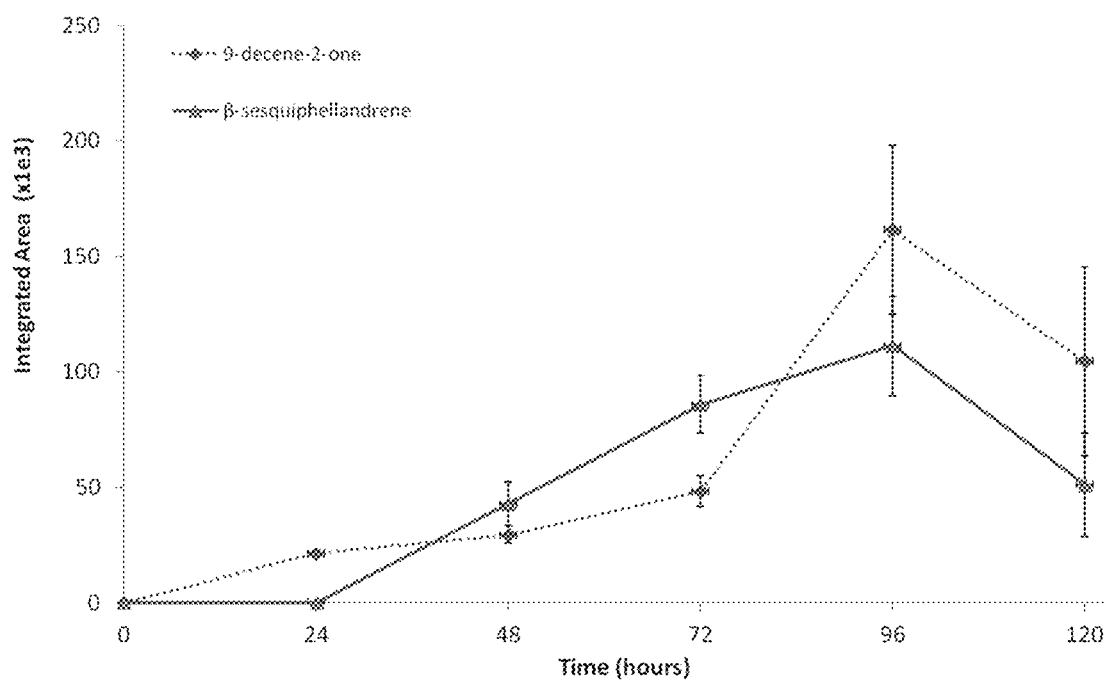
FIG. 8. Kinetics of *A. calidoustus* VOC emission with hyphal growth.

The key VOC features of *A. calidoustus* were first clearly discernible at 24-48 hours of incubation and reached their peak at 96 hours of incubation (FIG. 8).

Figure 9A:
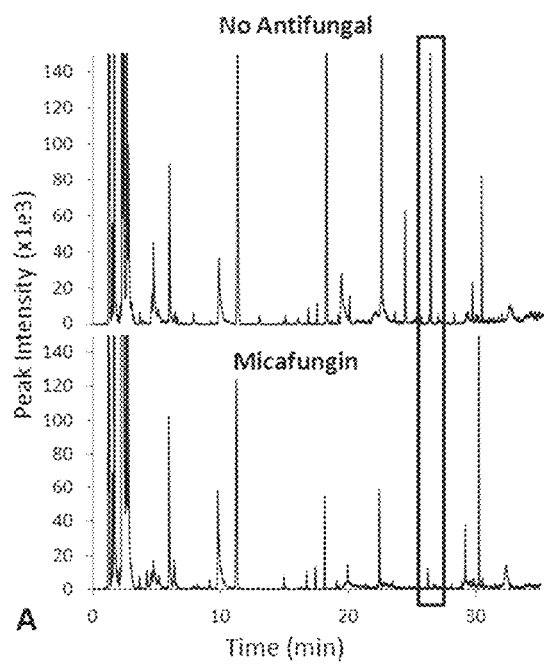
FIGS. 9A-B. Modulation of key *A. fumigatus* VOCs with antifungal therapy. A) GC-MS TIC of *A. fumigatus* with the addition of micafungin, showing initial increase in key VOCs at 24 hours. B) GC-MS TIC of *A. fumigatus* with the addition of voriconazole, showing near-complete attenuation in key VOCs at 24 hours.

Antifungal Exposure Modulates the Release of VOCs in *A. fumigatus*:

Whether exposure to antifungal drugs might modulate VOC release in *Aspergillus fumigatus* was assessed in vitro. When micafungin was added to 48-hour hyphal cultures of *A. fumigatus*, up to a 17-fold increase in some of the key *A. fumigatus* VOC features was observed after 24 hours, compared to matched control samples without micafungin (FIG. 9A); attenuation of these VOC features was observed with a longer duration of incubation and hyphal death. A similar initial increase then attenuation in key *A. fumigatus* VOCs was observed in response to liposomal amphotericin B.

Figure 9B:
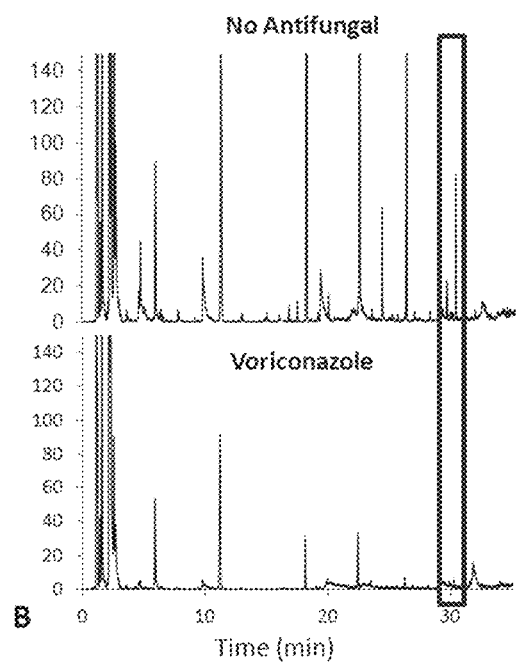

When voriconazole was added to 48-hour hyphal cultures of *A. fumigatus*, near-complete attenuation of the key VOC features of this species was observed after 24 hours, compared to matched control samples without voriconazole (FIG. 9B).

Figure 10A:
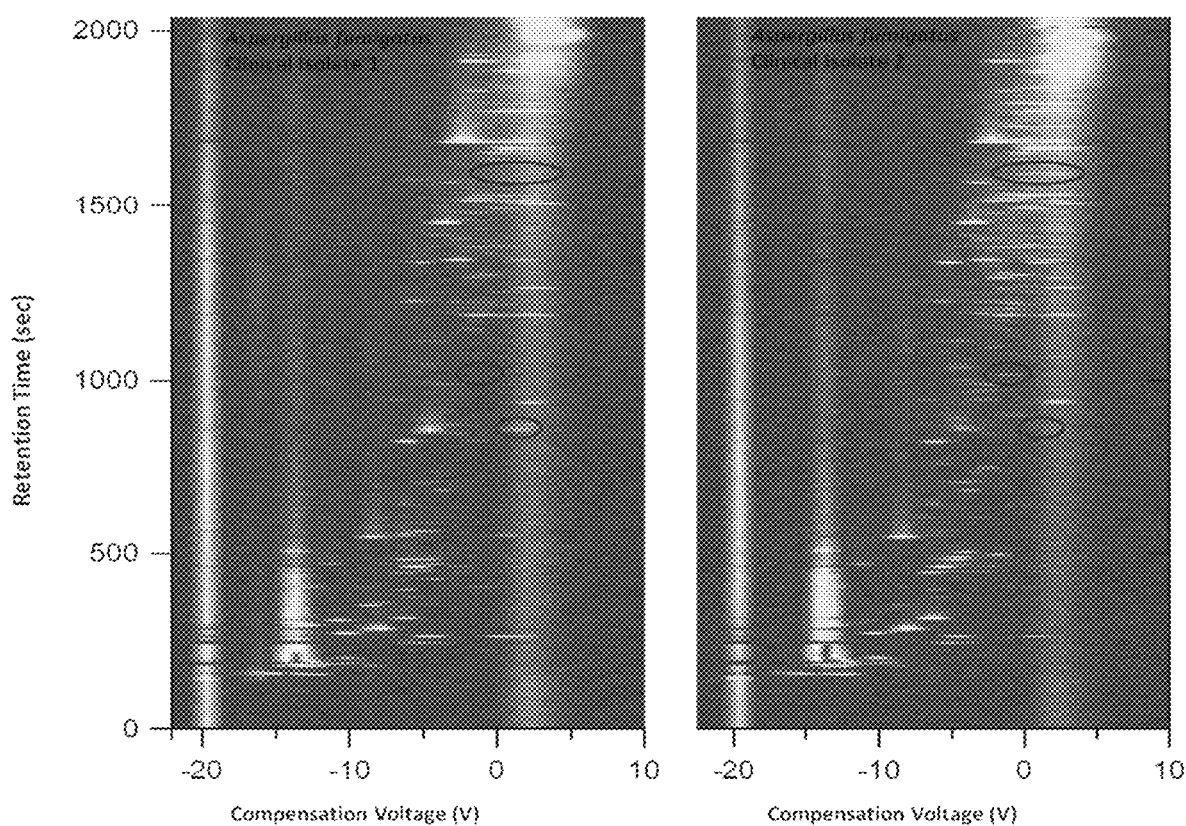
FIGS. 10A-B. Positive ion DMS spectra of *Aspergillus* species, showing A) Conservation of the DMS pattern between two members of *A. fumigatus*, and B) Conservation of the DMS pattern between two members of *A. terreus*. The DMS pattern is clearly different between *A. fumigatus* and *A. terreus*.
Figure 10B:
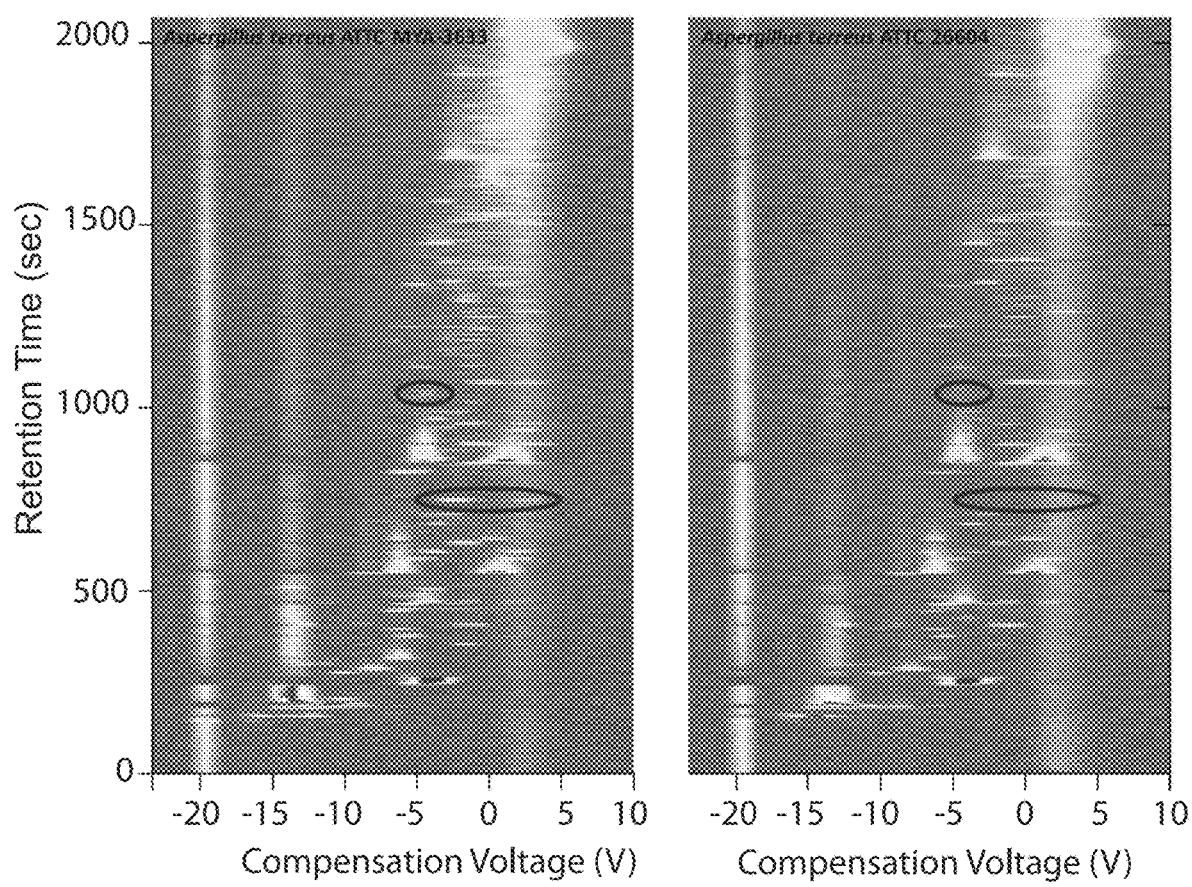

Definition of GC-Differential Mobility Spectrometer Patterns of *A. fumigatus* and *A. terreus*:

As a step towards utilizing portable GC-differential mobility spectrometry (DMS) technology as a point-of-care gas detector for *Aspergillus*, the eluent from the GC was split between a MS and a DMS device. DMS is an extremely sensitive and selective chemical detector that operates at atmospheric pressure with a small power source, allowing it to be used outside the laboratory for the detection of specific VOC patterns. DMS positive ion spectral features of headspace gas from *A. fumigatus* and *A. terreus* were examined. The DMS pattern was clearly conserved within members of each species and clearly distinct between *A. fumigatus* and *A. terreus* (FIG. 10A, 10B).

Figure 11A:
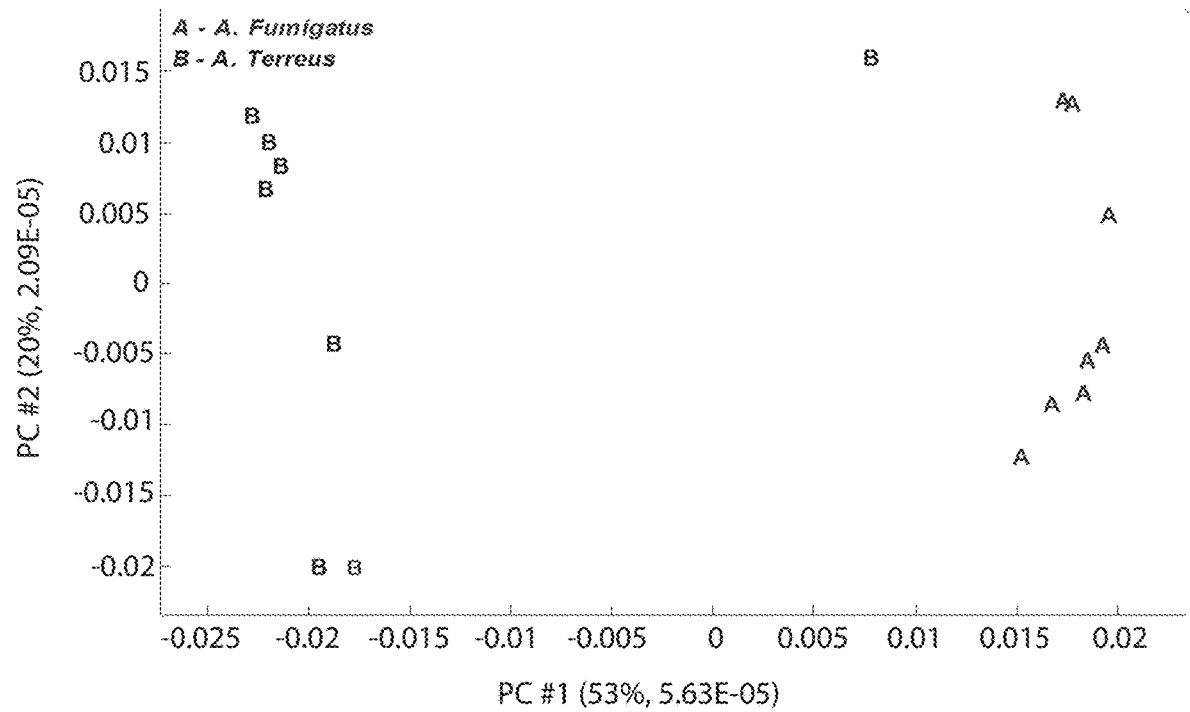
FIGS. 11A-B. Principal component analysis (PCA) score plots for *A. fumigatus* and *A. terreus*. 11A) Each letter represents an experimental replicate of type strains of *A. fumigatus* (A) and *A. terreus* (B). Percentage of total variance and absolute Eigenvalue are outlined in parentheses on each axis. There is clear clustering of *A. fumigatus* and *A. terreus* DMS features and separation between these species. 11B) Each letter represents an experimental replicate of clinical and culture collection strains of *A. fumigatus* (A, B) and *A. terreus* (C, D), with clear clustering within species and distinct separation between species.
Figure 11B:
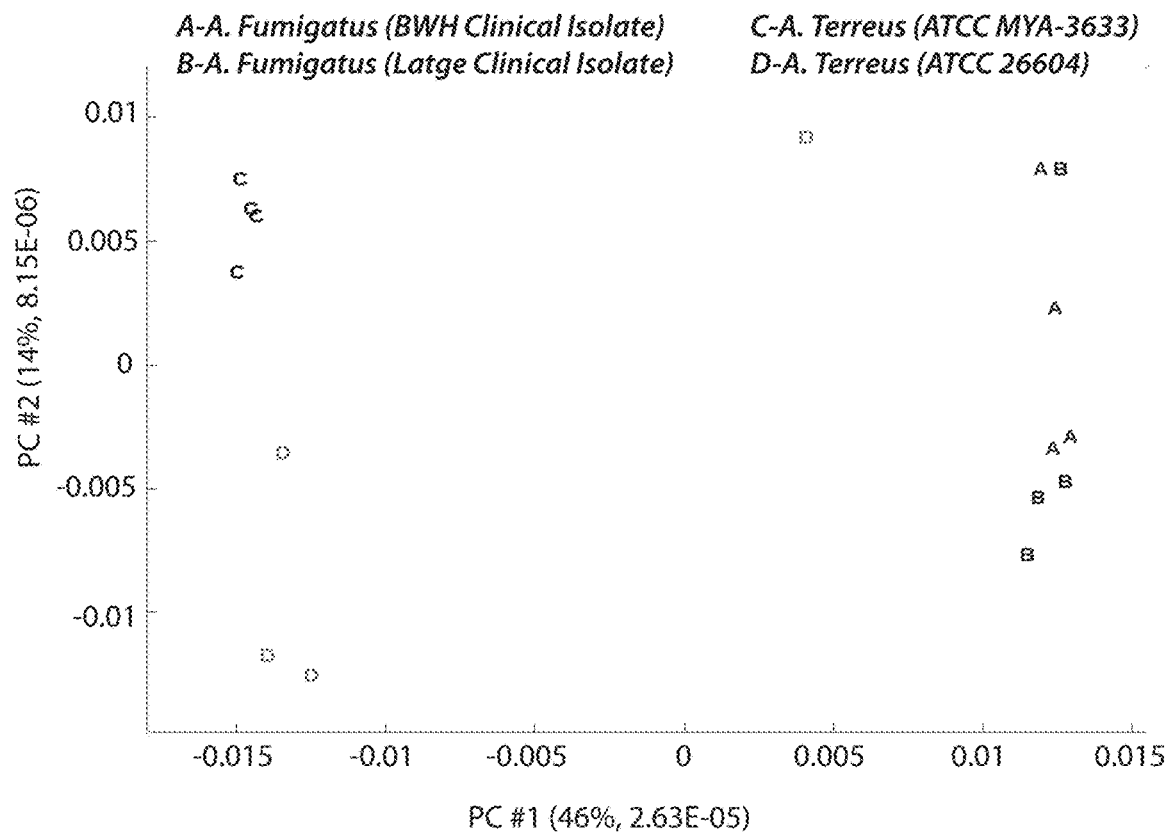

Using principal component analysis (PCA), the degree of class separation between *A. fumigatus* and *A. terreus* was evaluated. There was clustering of samples from the same species, and clear separation between *A. fumigatus* and *A. terreus* clusters (FIG. 11A, 11B).

Detection of *A. fumigatus* VOCs in Patient Breath:

Tidal breath was collected from 54 immunocompromised patients with suspected invasive aspergillosis to assess whether patients with IA could be distinguished from patients without IA by detecting fungal VOCs in their breath.

Of 54 patients, 23 (43%) were female, 46 (85%) had a hematologic malignancy, 22 (41%) allogeneic stem cell transplants, 6 (11%) solid organ transplants, 46 (85%) exposure to T-cell immunosuppressants, and 24 (44%) prolonged neutropenia. These characteristics were comparable in 29 patients with EORTC/MSG proven (3) or probable (26) IA and 25 patients with nodular pneumonia caused by other fungal infections or other infectious processes.

Figure 12:
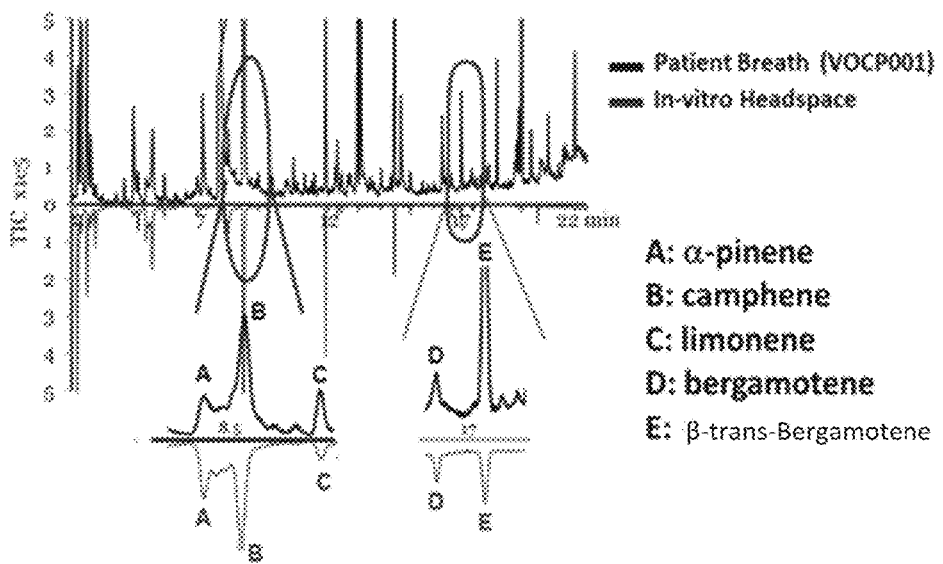
FIG. 12. Overlay of the GC-MS total ion chromatograph of a representative breath sample of a patient with invasive aspergillosis (black chromatogram) and an in vitro culture of *A. fumigatus* Af293 (inverted red chromatogram).

There was substantial overlap between the key *A. fumigatus* VOCs we identified in vitro and in the breath of patients with invasive aspergillosis (FIG. 12), although we also identified a new sesquiterpene compound, beta-vatirenene, and an oxidized terpene derivative, trans-geranylacetone, in the breath of patients with IA that were not induced by any of our in vitro culture conditions.

While some of the key VOCs identified in *A. fumigatus* in vitro were present equally in patients with and without IA, a combination of beta-trans-bergamotene and beta-vatirenene and the oxidized terpene derivative trans-geranylacetone distinguished patients with IA from patients without IA correctly in 51/54 (94%) patients (FIG. 13)—27 of 29 patients with IA (sensitivity=93%) and 24 or 25 patients who ultimately had other causes of pneumonia (sensitivity=96%). These VOCs were absent in ambient air control samples collected concurrently with each breath sample.

Breath was collected from a few patients serially following initiation of antifungal therapy and these key *A. fumigatus* VOCs appeared to decline over 1-2 weeks of treatment.

Example 2. A Breath Fungal Secondary Metabolite Signature to Diagnose Invasive Aspergillosis Objective:

To define the volatile metabolic profile of *Aspergillus fumigatus*, the most common cause of invasive aspergillosis, and assess whether patients with invasive aspergillosis can be distinguished from patients with other pneumonia by direct detection of fungal metabolites in their breath.

Design:

The study had two parts: A) An in vitro assessment of the volatile metabolite profile of pathogenic *Aspergillus* species, and B) Prospective collection of breath samples from individuals with suspected invasive aspergillosis from 2011-2013, with measurement of volatile metabolites of fungal origin using thermal desorption-gas chromatography/mass spectrometry.

Methods

*Aspergillus* Isolates: We characterized the in vitro VOC profile of the most common cause of IA, *Aspergillus fumigatus* (*A. fumigatus* Af293, *A. fumigatus* A1163, and 7 invasive clinical isolates). For comparison, we also investigated the in vitro VOC profiles of *A. terreus*, *A. flavus*, *A. niger*, and *A. calidoustus*, an emerging *Aspergillus* species with in vitro resistance to triazole antifungal drugs.[24, 25] Specific strains are listed online (Methods). The species identity of all strains was confirmed by ITS and β-tubulin sequencing at the Fungus Testing Laboratory at the University of Texas Health Science Center at San Antonio or at the Centers for Disease Control (CDC).[26]

Fungal Culture and Headspace Extraction Conditions:

Conidial suspensions were prepared in sterile water for each *Aspergillus* isolate. $10^4$ *A. fumigatus* conidia were inoculated into 5 mL of various liquid media in a 20 mL glass vial sealed with an airtight cap incorporating a silicone septum (Restek Corporation, Bellefonte, Pa.), with concurrent media controls. We used a range of liquid media, given the potential for substrate-dependent secondary metabolite production[27]—yeast extract-peptone-dextrose (YPD) broth (Teknova, Hollister, Calif.), *Aspergillus* minimal media,[28] and culture conditions that have been shown to generate *A. fumigatus* transcriptomes in vitro that overlap with its transcriptome in a murine lung infection model, including iron-limited, nitrogen depleted, and alkaline stress conditions[21]—in sets of 4 technical replicates for each *A. fumigatus* isolate. Each vial was incubated in an orbital shaker at 250 rpm to promote hyphal, rather than conidial, growth at 37° C. for 96 hours. Headspace gas in each vial was dynamically adsorbed over 2 minutes per sample, using argon carrier gas and an air sampling pump calibrated to 20 mL per minute, onto tandem thermal desorption tubes containing tandem sorbent beds of Tenax TA (200 mg), Carbograph 1 TD (100 mg), and Carboxen 1003 (100 mg) (Markes International, Llantrisant, United Kingdom), to retain polar and nonpolar VOCs over a wide range of boiling points.

We assessed whether we could modulate the *A. fumigatus* VOC metabolome with voriconazole, micafungin, and liposomal amphotericin B antifungal drug exposure, as described online (Methods). Headspace volatile metabolites of *A. terreus*, *A. flavus*, *A. niger*, and *A. calidoustus* were characterized as outlined above, in YPD broth at 96 hours.

Patients and Study Procedures:

Adult patients at Brigham and Women's Hospital and Dana-Farber Cancer Institute with suspected pulmonary IA, based on host risk factors, clinical symptoms, and radiologic findings suggestive of invasive fungal disease (IFD), were eligible for this breath collection study from November 2011 to September 2013. We were notified of patients with suspected IFD by inpatient and ambulatory oncology, transplant, and immunocompromised host infectious diseases care teams. Exclusion criteria were technical inability to provide a tidal breath sample and receipt of mechanical ventilation. Study participants provided written informed consent. Sixty-five of 67 consecutive individuals approached for this study provided written informed consent. One patient developed the acute onset of mental status changes shortly after providing informed consent and was unable to participate. This study was approved by the Partners Human Research Committee and the Office for Human Research Studies at the Dana-Farber Cancer Institute.

We prospectively collected tidal breath samples from each patient using a Programmable Breath Sampler (Gruppo Loccioni, Ancona, Italy), which displays real-time measurements of carbon dioxide and mouth pressure, allowing reproducibility of breathing patterns in each patient. We sampled four minutes of tidal breathing, with dynamic adsorption of breath VOCs using an air sampling pump calibrated to 900 mL per minute over the 4 minute period. Breath VOCs were adsorbed onto two parallel thermal desorption tubes made to the same specifications as the tubes we used for the in vitro experiments. Two samples of ambient air from each patient's inpatient or ambulatory room were collected concurrently with each breath sample using identical air sampling pump and thermal desorption tube parameters, to assess for environmental volatiles.

In addition to prospective collection of data on patient demographics and host, clinical, and mycology data required for an assessment of the likelihood of invasive fungal disease (IFD) in each patient, we recorded factors that might potentially cause spurious signals in each patient's breath VOC profile, including the time and contents of the last meal prior to breath sampling, tobacco use, and details of concurrent medication exposure.

Patients were classified as having 'proven,' 'probable,' or 'possible' IFD independently by two experts (SK and FMM) blinded to the volatile assessment, according to the revised European Organization for Research and Treatment of Cancer/Mycoses Study Group (EORTC/MSG) consensus criteria,[29] the current gold standard for diagnostic classification of patients with IFD. This assessment was performed ≥1 month after initial breath collection. Patients with 'proven' or 'probable' aspergillosis were considered true IA cases for the reference standard, while patients with 'possible' IFD or other fungal causes of 'proven' or 'probable' IFD were considered non-IA cases.

Thermal Desorption/Gas Chromatography-Mass Spectrometry:

For both in vitro culture headspace extractions and patient breath samples, VOCs were thermally desorbed using an automated thermal desorption unit interfaced to a gas chromatograph (GC)-mass spectrometer (MS), as outlined online (Methods).

Spectral Data Analysis:

We used the National Institute of Standards and Technology (NIST) 11 Mass Spectral Library (Scientific Instrument Services, Ringoes, N.J.) for provisional identification of each GC-MS peak in the total ion chromatogram of each in vitro culture, breath sample, and media or ambient air control. Analysis of VOCs in breath samples, including provisional identification of peaks and analysis of the integrated area of each peak, was performed by HRT and SDD without knowledge of patient IA status. The chemical identity of monoterpene and sesquiterpene peaks was verified with pure chemical standards of each key peak, where available, or against essential oils containing these compounds, as detailed online (Methods).

Statistical Analysis:

We used a Bayesian approach to the analysis of patient breath data, focusing on distinctive sesquiterpene volatile metabolites identified in the headspace of in vitro *A. fumigatus* cultures, and their derivatives. As we hypothesized a priori based on our in vitro experiments that these distinctive *A. fumigatus* VOCs would be entirely absent in individuals without IA, we assessed for the qualitative presence or absence of any of these volatile elements in each individual breath sample. We used the heatmap.2 function in the R gplots package[30] to plot the relative abundance of monoterpene and sesquiterpene metabolites and related compounds in the first breath of each study patient. We used the Mann-Whitney test and Fisher's exact test to assess the null hypothesis of no difference in clinical covariates between patients with IA and patients without IA and calculated two-tailed p-values. We calculated the sensitivity and specificity of *A. fumigatus* VOC metabolite signature for IA with exact binomial 95% confidence intervals (CI). We calculated positive and negative likelihood ratios and corresponding 95% CI.[31] We used Stata 11 (StataCorp LP, College Station, Tex.) for these analyses.

List of *Aspergillus* Isolates Characterized In Vitro:

We characterized the in vitro VOC profile of the most common cause of IA, *Aspergillus fumigatus* (*A. fumigatus* Af293, *A. fumigatus* A1163, and 7 invasive clinical isolates). For comparison, we also investigated the in vitro VOC profiles of *A. terreus* (*A. terreus* 601.65 (the type strain of *A. terreus* var. *terreus*) and 6 invasive clinical isolates from the Transplant-Associated Infection Surveillance Network [TRANSNET] (Balajee S A, Kano R, Baddley J W, et al. Molecular identification of *Aspergillus* species collected for the Transplant-Associated Infection Surveillance Network. J Clin Microbiol. 2009; 47(10):3138-3141)), *A. flavus*, *A. niger* (6 invasive clinical isolates each from TRANSNET), and an emerging *Aspergillus* species with in vitro resistance to triazole antifungal drugs, *A. calidoustus* (*A. calidoustus* 121601 (the holotype of *A. calidoustus*), and 2 invasive clinical isolates from TRANSNET) (Varga J, Houbraken J, Van Der Lee H A L, Verweij P E, Samson R A. *Aspergillus calidoustus* sp. nov., causative agent of human infections previously assigned to *Aspergillus ustus*. Eukaryot Cell. 2008; 7(4):630-638; Baddley J W, Marr Ka, Andes D R, et al. Patterns of susceptibility of *Aspergillus* isolates recovered from patients enrolled in the Transplant-Associated Infection Surveillance Network. J Clin Microbiol. 2009; 47(10):3271-3275).

Assessment of the *A. fumigatus* volatome response to antifungal drug exposure: For an assessment of *A. fumigatus* VOC response to antifungal drug exposure, $10^4$ *A. fumigatus* Af293 and A1163 conidia were inoculated into YPD broth and incubated at 37° C. at 250 rpm for 48 hours, then exposed to an inhibitory dose (1.0 μg/mL) of voriconazole (Pfizer Inc., New York, N.Y.), micafungin, liposomal amphotericin (both Astellas Pharma US, Inc., Northbrook, Ill.), or no antifungal therapy for 12 hours, in 4 technical replicates, with matched media controls exposed to the same conditions. VOCs in the headspace of each vial were extracted onto thermal desorption tubes. The cultures and media samples were incubated at 37° C. at 250 rpm for another 36 hours, with repeat extraction of the headspace gas onto thermal desorption tubes.

Thermal Desorption/Gas Chromatography-Mass Spectrometry Parameters:

After breath sampling, sorbent traps were sealed with airtight metal caps with Teflon ferrules (Swagelok, Solon, Ohio) and stored at 4° C. until thermal desorption. Most sorbent traps were desorbed within a few hours of patient breath sampling, although some sorbent traps were stored for up to one week before thermal desorption without appreciable loss of signal.

For both in vitro culture headspace extractions and patient breath samples, VOCs were thermally desorbed onto an automated thermal desorption unit (TD-100, Markes International) at 290° C. for 20 minutes with helium carrier gas at a flow rate of 40 mL per minute and concentrated onto a Unity2/TD-100 cold trap (U-15ATA-2S, Markes International). The cold trap was rapidly heated to 270° C. to deliver adsorbed VOCs (3.5:1 split) to a VF624 capillary column (30 m×0.32 mm, 6% cyanopropyl/phenyl, 94% polydimethylsiloxane, film thickness 1.8 μm, Agilent Technologies, Santa Clara, Calif.) with a gas chromatograph (GC) inlet temperature of 250° C. VOCs delivered to the capillary column were separated using a GC temperature program of 40° C. for 3 minutes, raised to 70° C. at a rate of 5° C. per minute and held for 3 minutes, raised to 203° C. at 7° C. per minute and held for 4 minutes, then rapidly raised to 270° C. and held for 5 minutes. A single quadrupole mass spectrometry (MS) detector (Agilent 5975, Agilent Technologies, Santa Clara, Calif.) was used to analyze and identify VOCs, with a MS source temperature of 230° C., MS quad temperature of 150° C., and an electron ionization parameter of 1412 eV. A mass range m/z 40-400 was measured with a threshold of 150.

Confirmation of Compound Identity: We used the National Institute of Standards and Technology (NIST) 11 Mass Spectral Library (Scientific Instrument Services, Ringoes, N.J.) for provisional identification of GC-MS peaks in the total ion chromatogram of each culture, breath sample, and media or ambient air control.

The chemical identity of monoterpene and sesquiterpene peaks was verified by spiking pure chemical standards of each key peak (α- and β-pinene, limonene, camphene (all Sigma-Aldrich, St. Louis, Mo.), and β-trans-bergamotene (gift of Drs. Hsiao-Ching Lin and Yi Tang; Lin H-C, Chooi Y-H, Dhingra S, Xu W, Calvo A M, Tang Y. The fumagillin biosynthetic gene cluster in *Aspergillus fumigatus* encodes a cryptic terpene cyclase involved in the formation of β-trans-bergamotene. J Am Chem Soc. 2013; 135(12):4616-4619)) in 96-hour *A. fumigatus* cultures, with confirmation of augmentation of our provisionally identified peak compared to an unspiked culture and a matching fragmentation pattern. The chemical identity of α-trans-bergamotene was confirmed by GC-MS analysis of bergamot oil (Sigma-Aldrich, St. Louis, Mo.), with retention time and fragmentation pattern matching between our provisionally identified peak and α-trans-bergamotene in the essential oil. The identity of trans-geranylacetone was confirmed by GC-MS analysis of a geranylacetone standard (Sigma-Aldrich, St. Louis, Mo.), with spectral and retention time matching to our compound. We attempted to confirm the identity of the breath sesquiterpene metabolite identified by the NIST library as β-vatirenene by GC-MS analysis of vetivert essential oil (Nature's Alchemy, Twin Lakes, Wis.) (Chou S-T, Lai C-P, Lin C-C, Shih Y. Study of the chemical composition, antioxidant activity and anti-inflammatory activity of essential oil from *Vetiveria zizanioides*. Food Chem. 2012; 134(1):262-268).

Results

Figure 15:
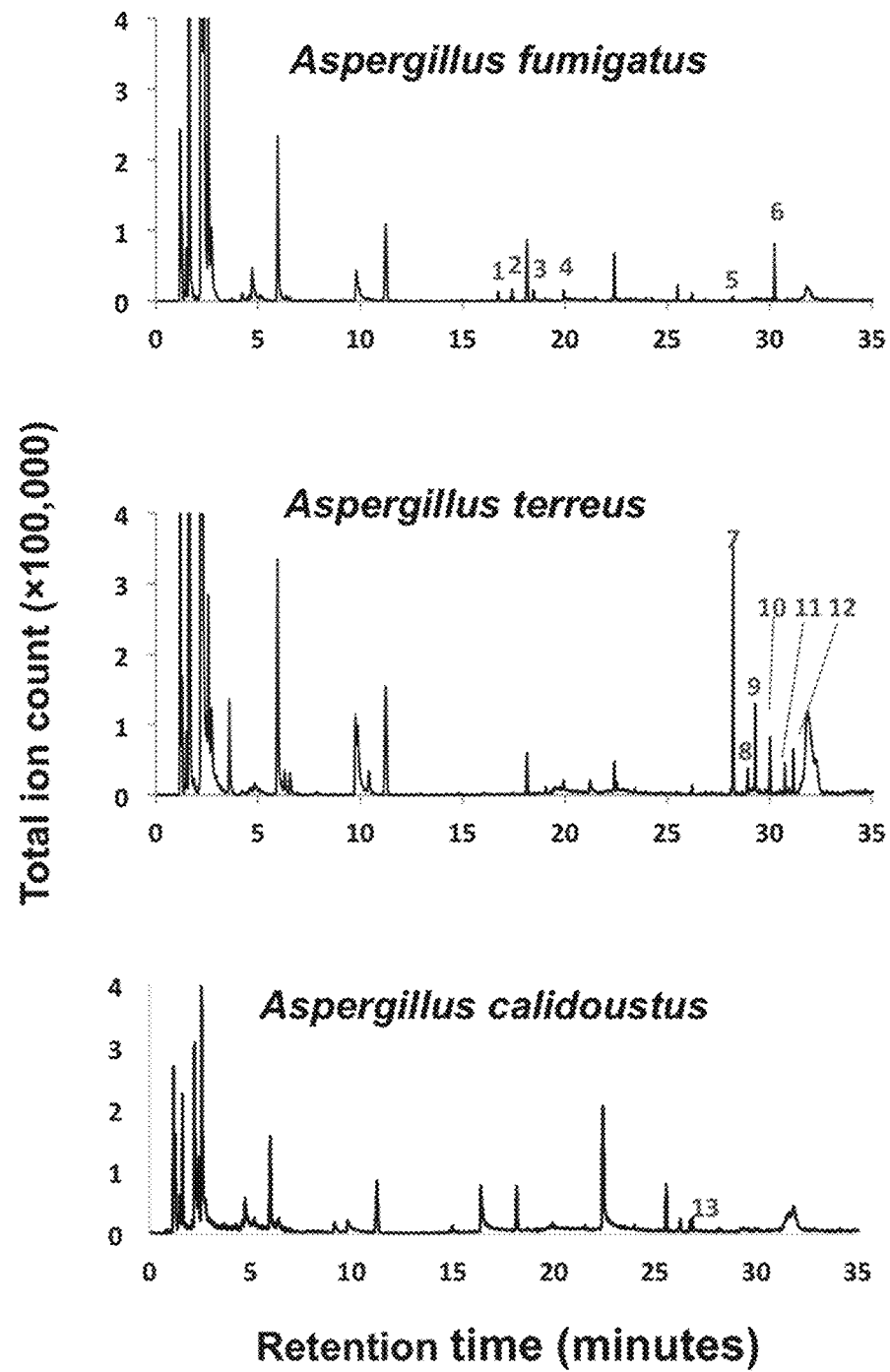
FIG. 15. In Vitro Volatile Organic Compound Profiles of *Aspergillus fumigatus* and Other Pathogenic *Aspergillus* Species. *Aspergillus* species have species-specific volatile organic compound profiles, with particular interspecies heterogeneity in monoterpene and sesquiterpene metabolites. The following peaks identified as 1) α-pinene; 2) β-pinene; 3) Camphene; 4) Limonene; 5) α-trans-bergamotene; 6) β-trans-bergamotene; 7) Elixene; 8) Santalene; 9) Elemene, 10) Acoradien 11) 1,5,9-trimethyl-1,5,9-cyclododecatriene; 12) Chamigrene; 13.) β-sesquiphellandrene.
Figure 16A:
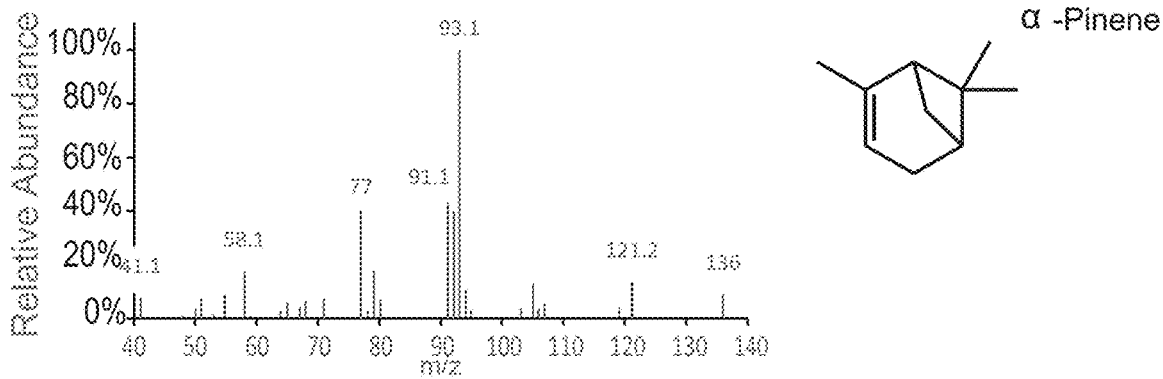
FIGS. 16A-O. Chemical structures and fragmentation patterns of key terpene Compounds. A) GC-MS spectrum and structure of α-pinene from *A. fumigatus*; B) GC-MS spectrum and structure of β-pinene from *A. fumigatus*; C) GC-MS spectrum and structure of camphene from *A. fumigatus*; D) GC-MS spectrum and structure of limonene from *A. fumigatus*; E) GC-MS spectrum and structure of trans-α-bergamotene from *A. fumigatus*; F) GC-MS spectrum and structure of trans-β-bergamotene from *A. fumigatus*; G) GC-MS spectrum and structure of elixene from *A. terreus*; H) GC-MS spectrum and structure of santalene from *A. terreus*; I) GC-MS spectrum and structure of elemene from *A. terreus*; J) GC-MS spectrum and structure of acoradien from *A. terreus*; K) GC-MS spectrum and structure of 1,5,9-trimethyl-1,5,9-cyclododecatriene from *A. terreus*; L) GC-MS spectrum and structure of chamigrene from *A. terreus*; M) GC-MS spectrum and structure of β-sesquiphellandrene from *A. calidoustus*; N) GC-MS spectrum and structure of β-vatirenene from breath samples of patients with *A. fumigatus* invasive aspergillosis; and O) GC-MS spectrum and structure of trans-geranylacetone from breath samples of patients with *A. fumigatus* invasive aspergillosis.
Figure 16B:
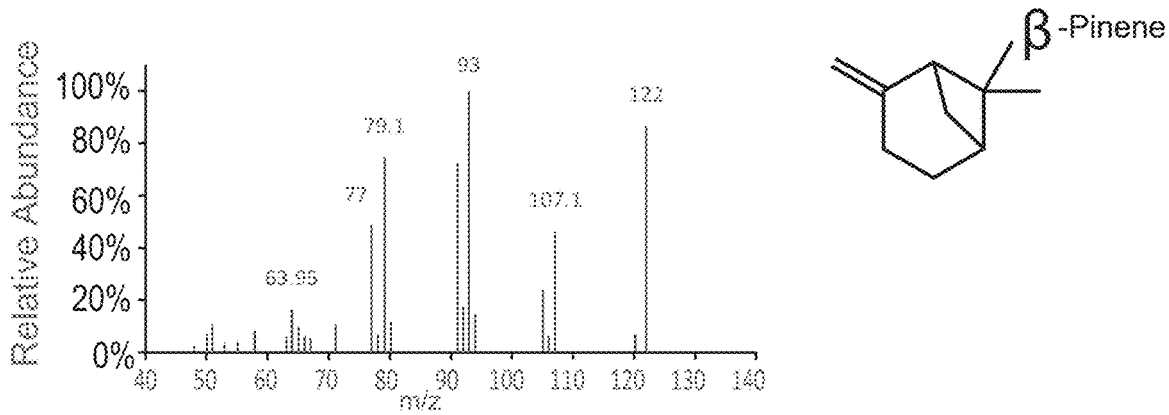
Figure 16C:
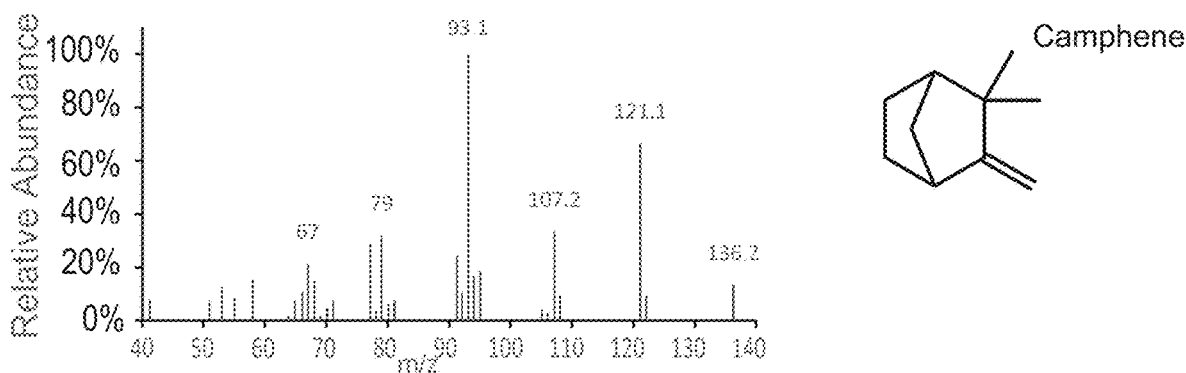
Figure 16D:
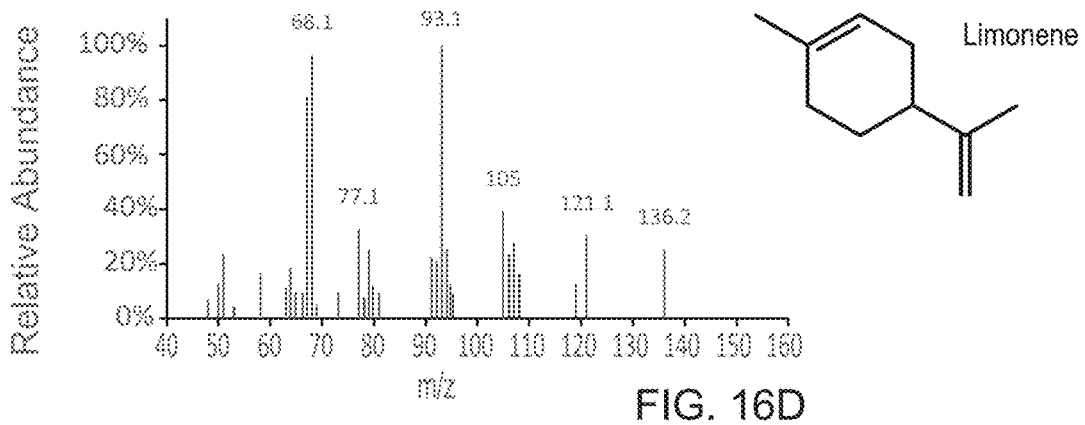
Figure 16E:
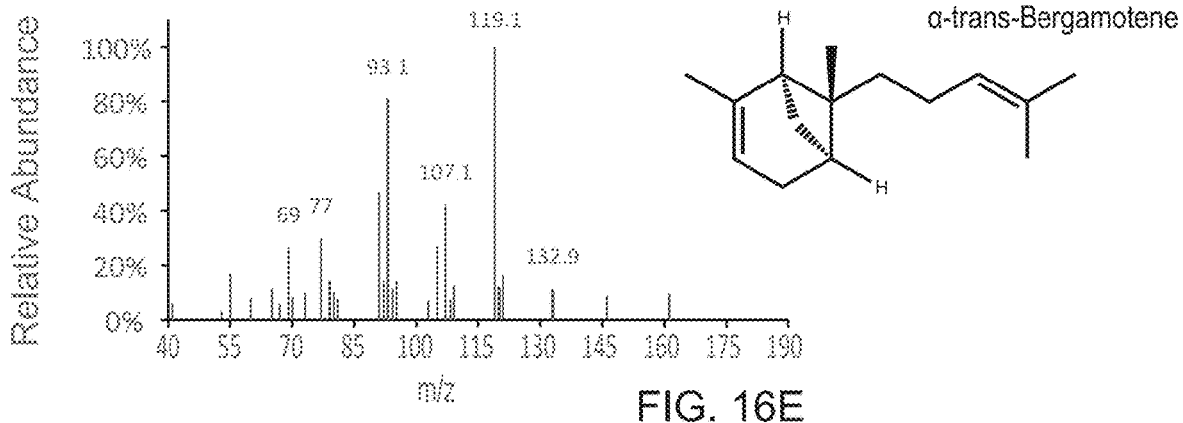
Figure 16F:
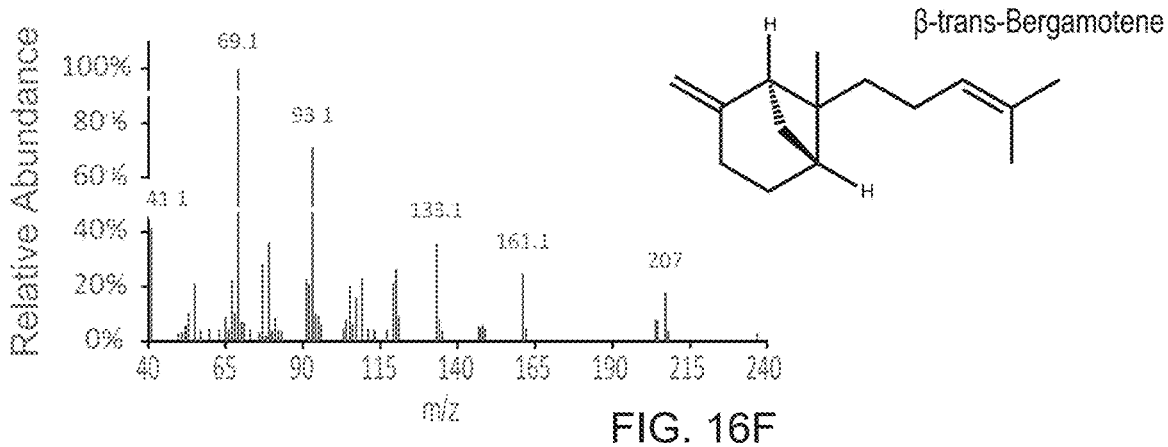
Figure 16G:
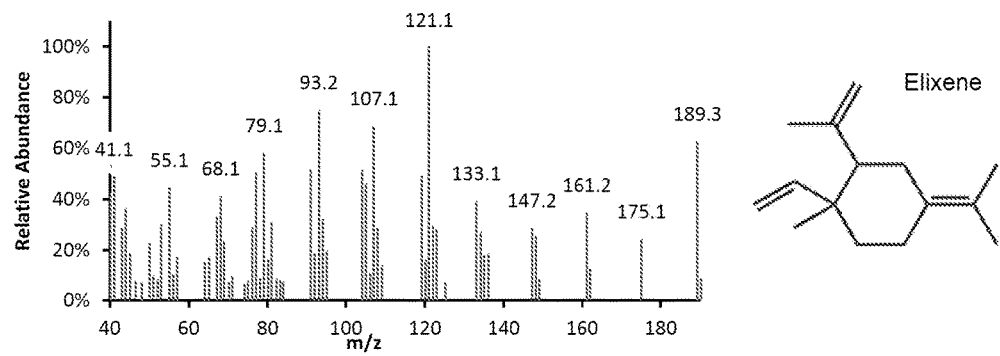
Figure 16H:
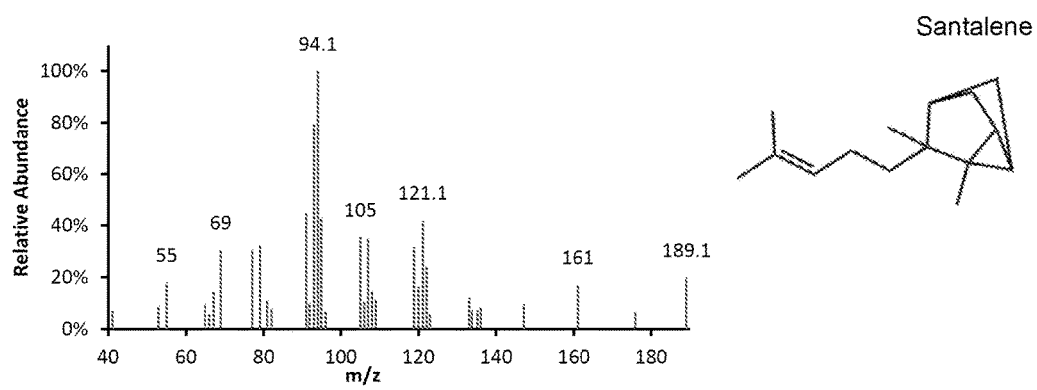
Figure 16I:
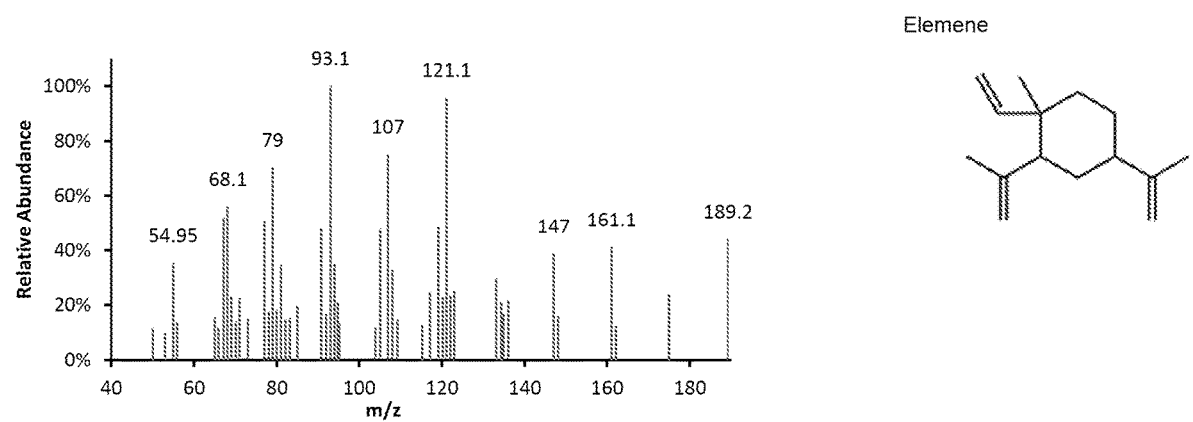
Figure 16J:
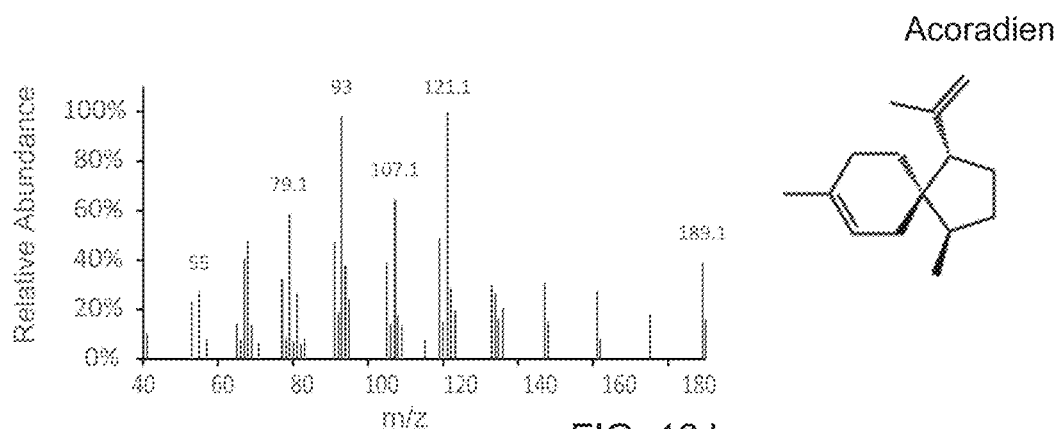
Figure 16K:
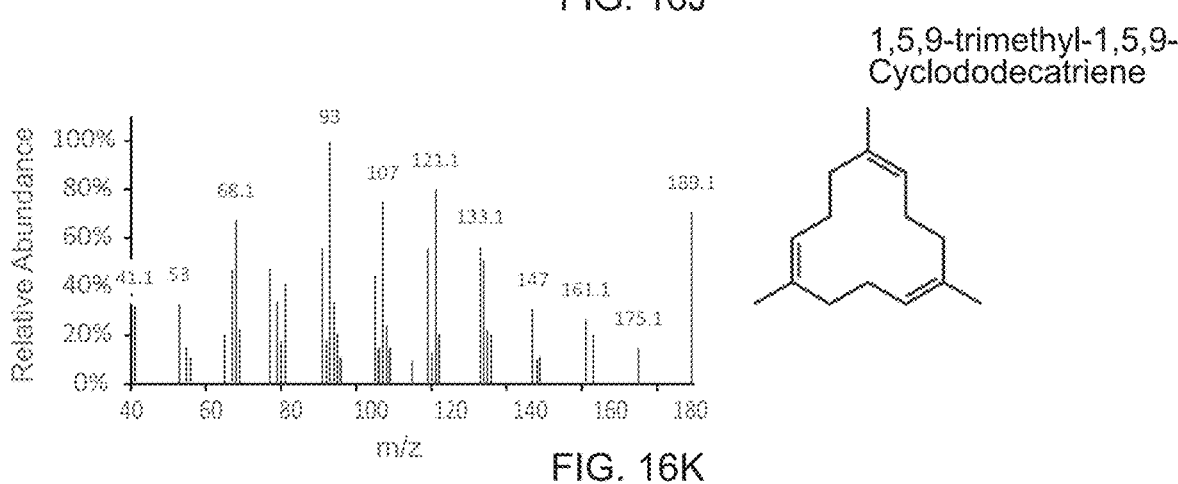
Figure 16L:
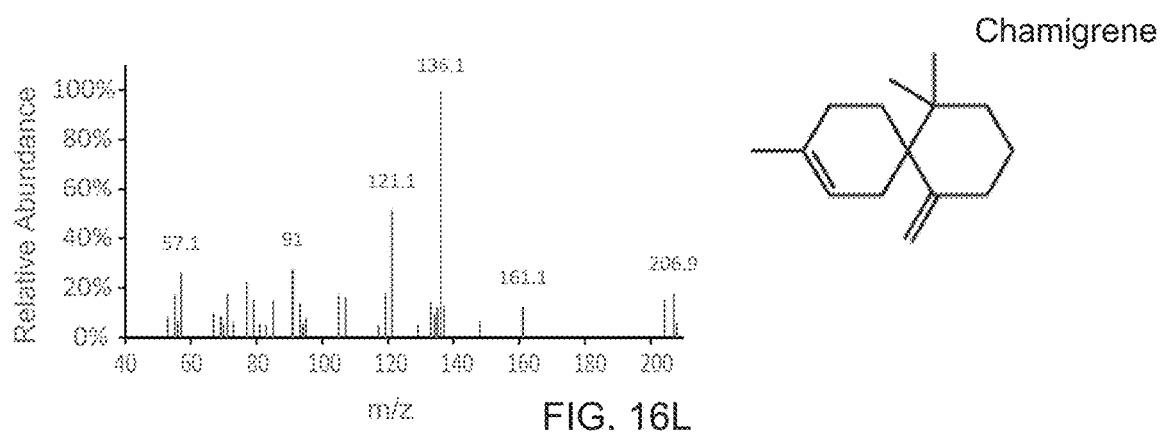
Figure 16M:
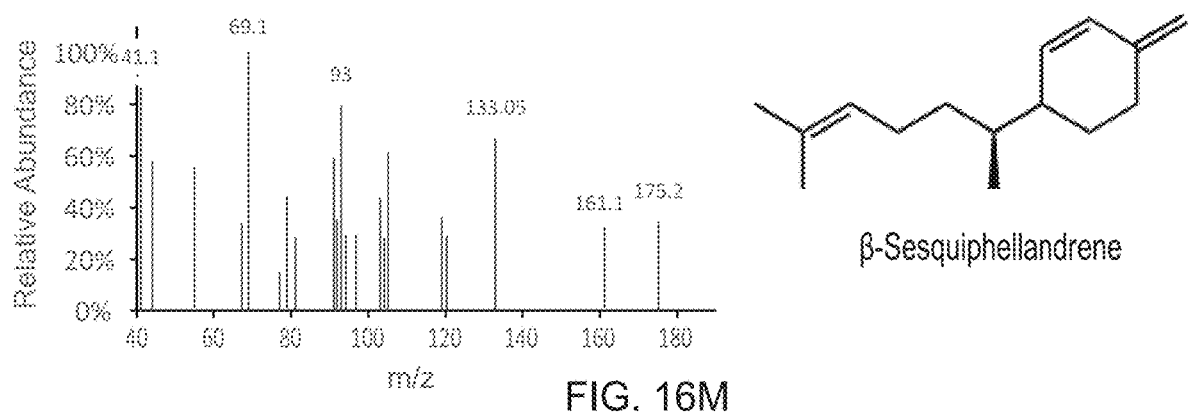
Figure 16N:
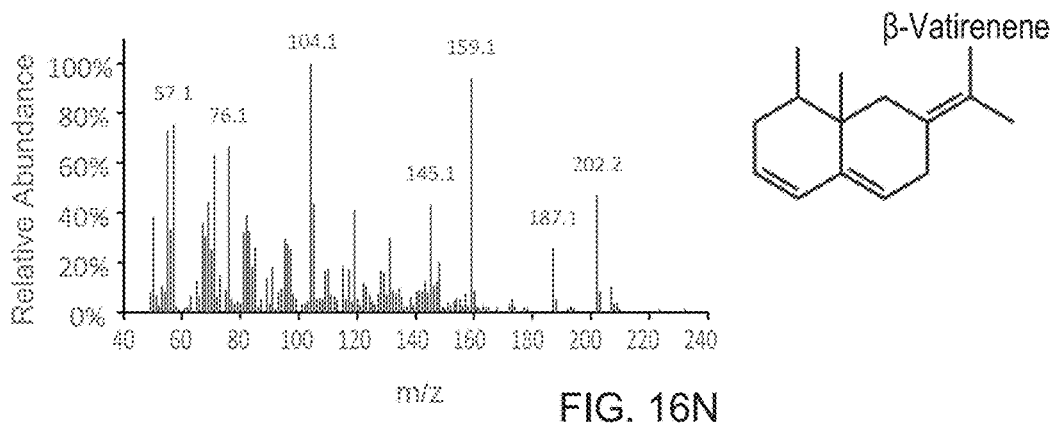
Figure 16O:
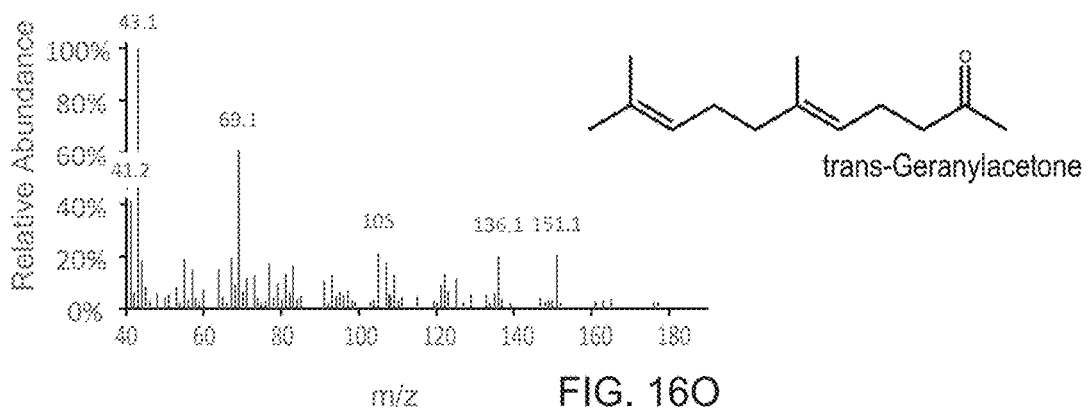
Figure 17A:
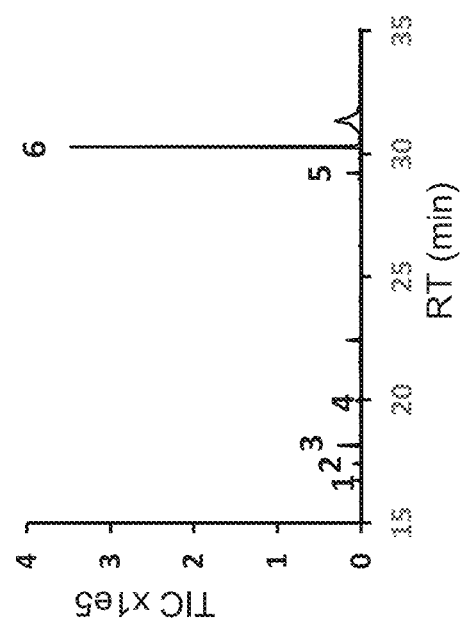
FIGS. 17A-D. Effect of nitrogen starvation, alkaline stress, and iron deprivation stress conditions on the volatile organic compound profile of *A. fumigatus* Af293. GC-MS analysis of *A. fumigatus* Af293 cultured for 96 hrs in (A) nutrient-rich YPD media, (B) nitrogen starvation, (C) alkaline stress, and (D) iron depletion (McDonagh A, Fedorova N D, Crabtree J, et al. Sub-telomere directed gene expression during initiation of invasive aspergillosis. PLoS Pathog. 2008; 4(9):e1000154). Labeled peaks were identified as 1) α-Pinene; 2) β-Pinene; 3) Camphene; 4) Limonene; 5) α-trans-bergamotene; 6) β-trans-bergamotene. TIC, total ion count; RT, retention time.
Figure 17B:
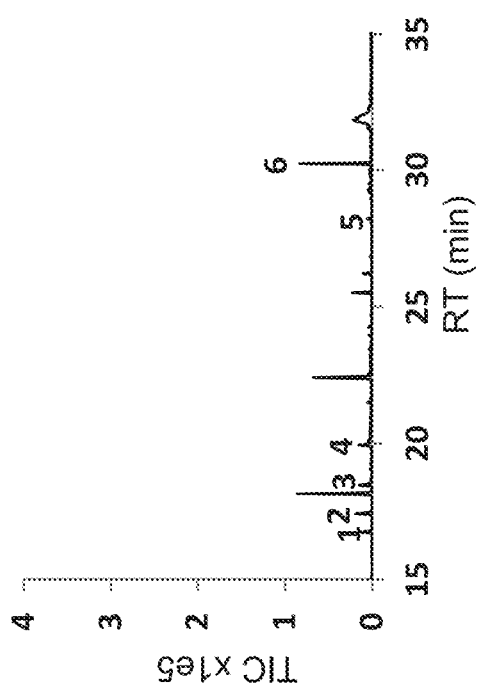
Figure 17C:
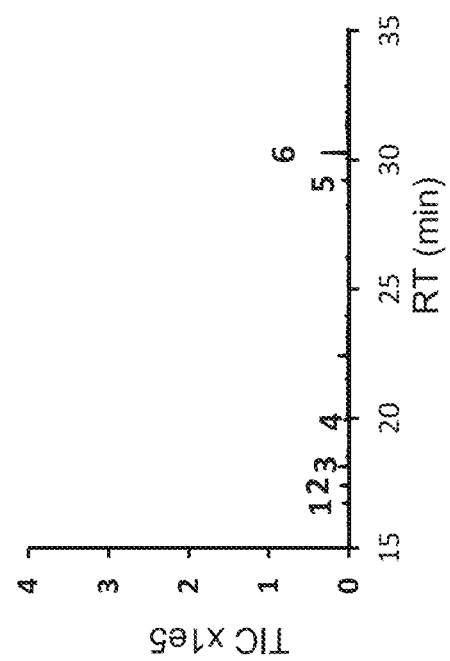
Figure 17D:
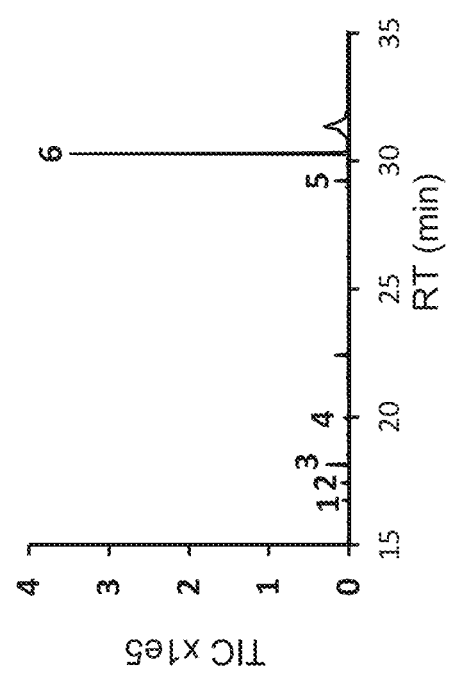

In Vitro VOC Profile of *Aspergillus fumigatus*:

The volatile monoterpene secondary metabolites camphene, α-pinene, β-pinene, and limonene, and sesquiterpene metabolites α-trans-bergamotene and β-trans-bergamotene were distinctive and prominent features of *A. fumigatus* (FIGS. 15 and 16A-O), consistent in all biologic replicates of *A. fumigatus*. Growth in *Aspergillus* minimal media or under iron-limited, nitrogen depleted, or alkaline stress conditions did not induce the production of any new VOCs. Iron-limited conditions attenuated monoterpene and sesquiterpene production, while nitrogen starvation and alkaline stress enhanced β-trans-bergamotene production (FIGS. 17A-D).

Exposure of *A. fumigatus* hyphae to antifungal drugs modulated VOC production, particularly sesquiterpenes: β-trans-bergamotene increased 10-fold from baseline with 12 hours of micafungin exposure, and 3-fold with 12 hours of liposomal amphotericin exposure, followed by near-complete attenuation of all volatile metabolites 36 hours later. In vitro voriconazole exposure, in contrast, reduced primary metabolite, monoterpene, and sesquiterpene production at 12 hours, with attenuation of all volatile metabolites 36 hours later (FIGS. 18A-D).

Figure 19:
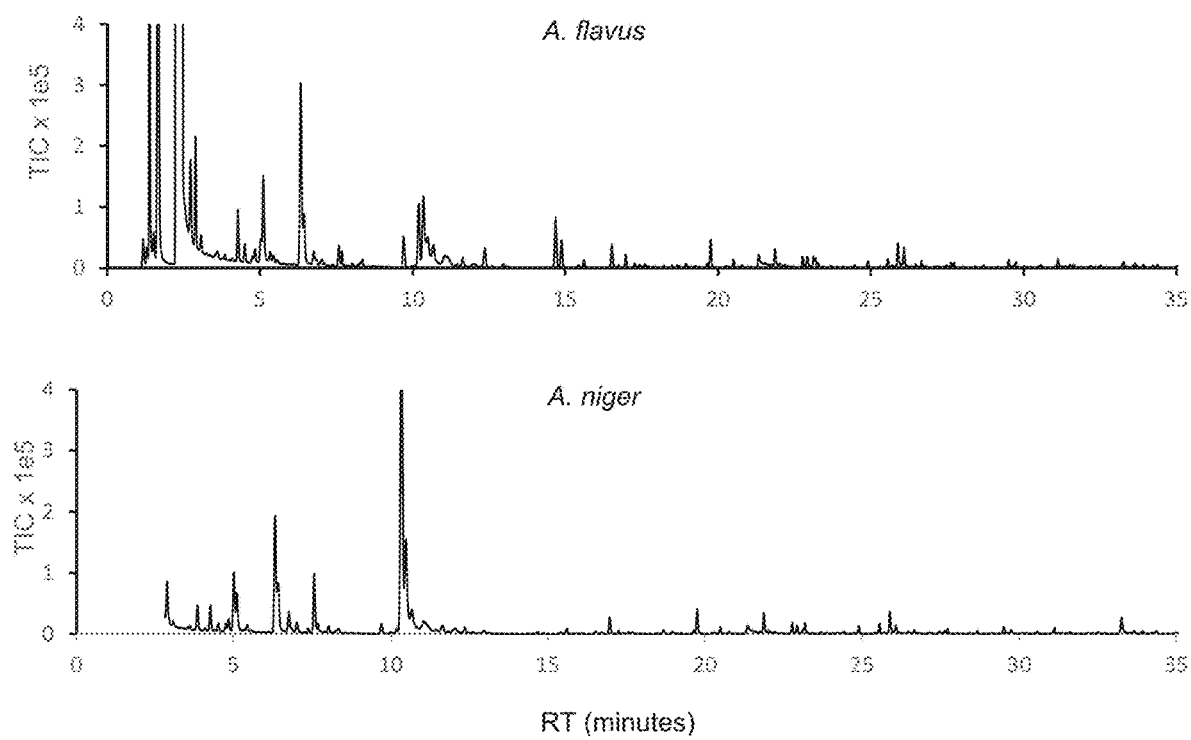
FIG. 19. In vitro volatile organic compound profiles of *Aspergillus flavus* and *Aspergillus niger*. GC-MS analysis of the headspace of 104 conidia of *A. flavus* and *A. niger* grown for 96 hours in YPD media. No sesquiterpene metabolites were identified under these growth conditions. TIC, total ion count; RT, retention time.

Distinct VOC Profiles of Other *Aspergillus* Species:

Each *Aspergillus* species we tested had a species-specific VOC profile, consistent within biological replicates of each species and distinct between species, with particular inter-species heterogeneity in monoterpene and sesquiterpene metabolites (FIG. 15). *A. terreus* (FIGS. 15 and 16A-O) had a particularly rich and abundant profile of sesquiterpene secondary metabolites, and *A. calidoustus* (FIGS. 15 and 16A-O) consistently produced β-sesquiphellandrene. Under these culture conditions, *A. flavus* and *A. niger* produced alcohols and ketones in abundance, but no volatile secondary metabolites other than limonene (FIG. 19). Other than limonene, there was no monoterpene or sesquiterpene overlap between *A. fumigatus* and any of the other pathogenic Aspergilli assessed.

A Volatile *A. fumigatus*-Specific Secondary Metabolite Signature in the Breath of Patients with Invasive Aspergillosis:

Of 64 consecutive patients with suspected IFD, comprising a heterogeneous group of patients with underlying hematologic malignancy, allogeneic hematopoietic stem-cell transplantation, and solid organ transplantation (Table 1), 34 were ultimately diagnosed with IA and 30 with other types of pneumonia, including other IFD (Table 2). Most patients had received empiric or prophylactic mold-active antifungal therapy for a median of 2 days prior to breath sampling (Table 1). There were no adverse events related to the breath collection procedure.

TABLE 1

Patient Characteristics

| Clinical Variable | Invasive Aspergillosis (N = 34) | Other Pneumonia (N = 30) | p-value |
|---|---|---|---|
| Median age, years (IQR; range) | 55 (47, 62; 22, 79) | 54 (44, 63; 28, 87) | 0.92 |
| Female gender, N (%) | 17 (50%) | 8 (27%) | 0.07 |
| Hematologic malignancy, N (%) | 29 (85%) | 24 (80%) | 0.74 |
| Allogeneic hematopoietic stem-cell transplantation, N (%) | 18 (53%) | 7 (27%) | 0.02 |
| Solid organ transplantation, N (%) | 3 (9%) | 5 (17%) | 0.46 |
| Recent neutropenia*, N (%) | 13 (38%) | 15 (50%) | 0.45 |
| T-cell immunosuppressants†, N (%) | 29 (85%) | 26 (87%) | 0.58 |
| Prolonged corticosteroid exposure‡, N (%) | 7 (21%) | 5 (17%) | 0.45 |
| Exposure to mold-active antifungal therapy on date of breath sampling§, N (%) | 25 (74%) | 26 (87%) | 0.23 |

TABLE 1-continued

Patient Characteristics

| Clinical Variable | Invasive Aspergillosis (N = 34) | Other Pneumonia (N = 30) | p-value |
|---|---|---|---|
| Duration of mold-active antifungal exposure prior to breath sampling, days, median (IQR; range) | 2 (2, 11; 1, 205) | 2 (1, 13; 1, 345) | 0.52 |

*<500 neutrophils/mm$^3$ for >10 days.[29]

†Treatment with recognized T-cell immunosuppressants, such as cyclosporine, TNF-α blockers, specific immunomodulating antibodies, or nucleoside analogues during the prior 90 days.[29]

‡Exposure to corticosteroids at a mean minimum dose of 0.3 mg/kg/day of prednisone equivalent for >3 weeks.[29]

§Specific antifungal agents included: voriconazole (N = 17), micafungin (N = 15), liposomal amphotericin B (N = 11), terbinafine (N = 1), isavuconazole (N = 1), voriconazole and micafungin (N = 2), voriconazole and terbinafine (N = 2), posaconazole and liposomal amphotericin B (N = 1), and fluconazole (N = 1) in a patient with suspected cryptococcal pneumonia.

TABLE 2

Invasive Fungal Disease Classification

Invasive Aspergillosis (N = 34)
  5 proven invasive aspergillosis
  29 probable invasive aspergillosis*
    18 serum galactomannan index ≥0.5
    4 *Aspergillus* species in respiratory tract cultures
    4 serum galactomannan index ≥0.5 and *Aspergillus* spp. in respiratory tract cultures
    3 bronchoalveolar lavage fluid galactomannan index ≥0.5
Other Pneumonia (N = 30)
  8 proven invasive fungal disease
    4 Mucorales
    1 *Cryptococcus neoformans*
    1 *Fusarium proliferatum*
    1 *Pseudalleseheria boydii*
    1 unidentified invasive dematiaceous mold on lung biopsy
  2 probable invasive fungal disease
    1 *Paecilomyces variotii*
    1 *Histoplasma capsulatum*
  20 possible invasive fungal disease†

*One patient had concurrent probable invasive aspergillosis and *Pneumocystis jirovecii* pneumonia.
†*Streptococcus pneumoniae* pneumonia (N = 1), *Stenotrophomonas maltophilia* pneumonia (N = 1), methicillin-resistant *Staphylococcus aureus* septic pulmonary emboli (N = 1), coagulase-negative *staphylococcus* septic pulmonary emboli (N = 1), and *Enterococcus faecalis* septic pulmonary emboli (N = 1). The specific underlying cause of pneumonia in the remaining 15 patients was not identified.

Figure 13:
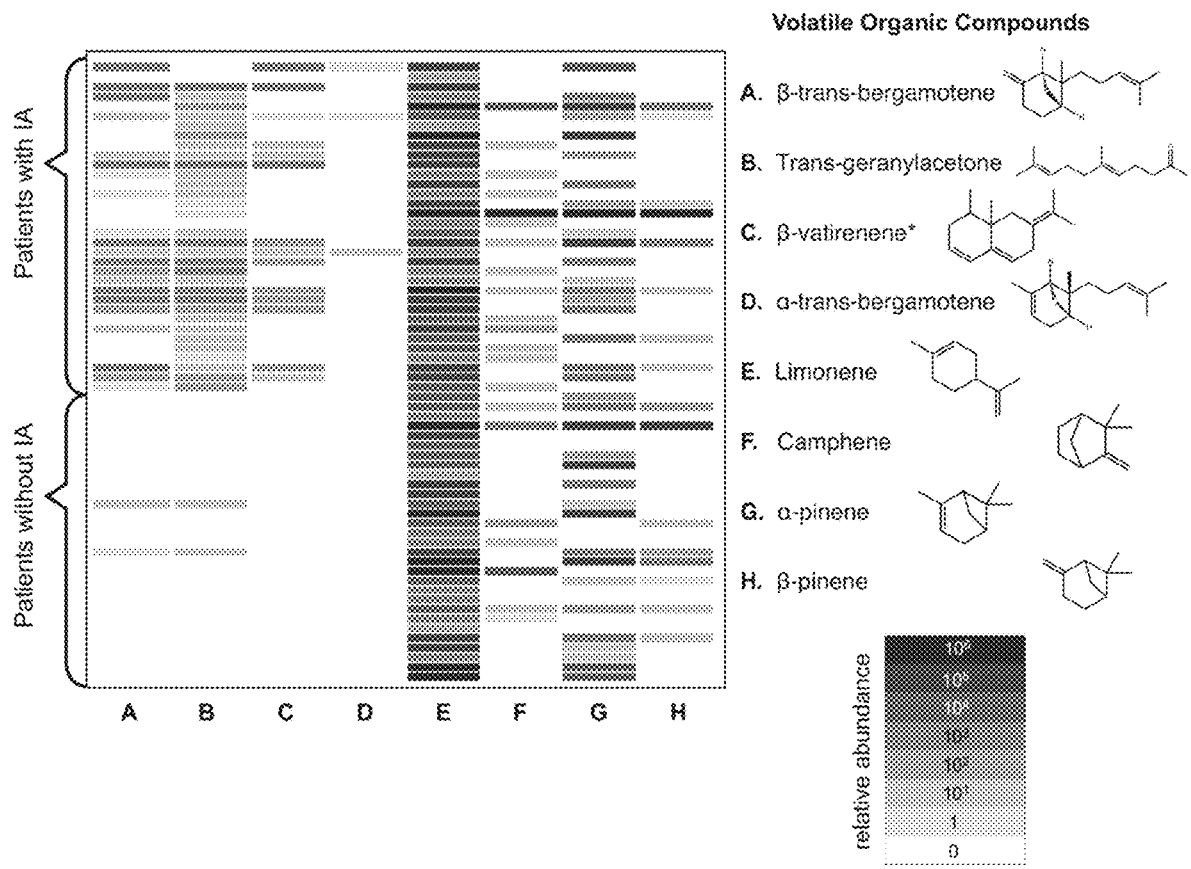
FIG. 13. This heatmap shows the average integrated area of terpene metabolites (columns A-H), showing the relative abundance of each key *A. fumigatus* VOC in the breath of patients with IA and patients without IA. Each row represents an individual patient's breath and each column represents one of the key *A. fumigatus* VOCs.

While monoterpene metabolites produced in vitro by *A. fumigatus* (camphene, α-pinene, β-pinene, and limonene) were equally present in the breath of patients with or without IA, the volatile sesquiterpene secondary metabolites β-trans-bergamotene and α-trans-bergamotene and two related metabolites that we did not observe in vitro, the terpenoid ketone trans-geranylacetone and a β-vatirenene-like sesquiterpene, distinguished the breath of patients with IA from patients without IA (FIG. 13). No sesquiterpene compounds were present in ambient air control samples. This *A. fumigatus* secondary metabolite signature distinguished patients with IA from patients with other IFD or other types of pneumonia with 94% (95% CI 81%-98%) sensitivity and 93% (95% CI 79%-98%) specificity utilizing the reference standard of proven or probable IA by EORTC/MSG consensus criteria (Table 3). The smallest lesion we detected through breath metabolite analysis was 0.88 cm$^3$ in a lung transplant patient with probable IA.

TABLE 3

Breath *Aspergillus fumigatus* Metabolite Signature by the Reference Standard and Test Parameters

|  | Invasive Aspergillosis | Other Pneumonia |  |
|---|---|---|---|
| *A. fumigatus* metabolite signature + | 32 | 2 | 34 |
| *A. fumigatus* metabolite signature − | 2 | 28 | 30 |
|  | 34 | 30 | 64 |
| Test Parameters | | | |
| Sensitivity (95% CI) | 0.94 (0.81, 0.98) | | |
| Specificity (95% CI) | 0.93 (0.79, 0.98) | | |
| Positive Likelihood Ratio (95% CI) | 14.1 (3.69, 54.0) | | |
| Negative Likelihood Ratio (95% CI) | 0.063 (0.02, 0.24) | | |

*A. niger*, which emits a distinct VOC profile from *A. fumigatus* in vitro (FIGS. 18A-D), was ultimately identified as the causal etiology of pneumonia in one of the two patients with 'probable' IA whose breath sample lacked the *A. fumigatus* volatile secondary metabolite signature. Interestingly, we detected a novel sesquiterpene compound in this patient's breath that we did not detect in the headspace gas of in vitro cultures of this patient's fungal isolate. On the other hand, there are limitations of the EORTC/MSG reference standard for the diagnosis of IA, which relies on the sensitivity of fungal antigens and cultures for the classification of 'probable' IA.[29] One patient with breath β-trans-bergamotene and trans-geranylacetone was classified as having 'possible' IFD during his lifetime, with pulmonary nodules but unrevealing respiratory tract cultures and negative fungal antigen testing. On autopsy, however, these pulmonary nodules contained invasive septate hyphal forms with acute-angle branching, which were identified as *Aspergillus* by immunohistochemical staining by the CDC Infectious Diseases Pathology Branch.

We found no association between the contents of the last meal prior to breath sampling, tobacco use, concurrently administered inhaled, oral, or topical medications and detection of this *Aspergillus* volatile secondary metabolite signature.

Antifungal Exposure Experiments.

Patients were evaluated over time to determine the response to antifungal therapy; the *A. fumigatus* metabolite signature described herein was evaluated over time as follows.

We assessed whether we could modulate the *A. fumigatus* VOC metabolome with voriconazole, micafungin, and liposomal amphotericin B antifungal drug exposure. We inoculated 10$^4$ *A. fumigatus* Af293 and A1163 conidia into YPD broth and incubated these cultures at 37° C. at 250 rpm for 48 hours, then exposed these 48 hour hyphae to an inhibitory dose (1.0 μg/mL) of voriconazole (Pfizer Inc., New York, N.Y.), micafungin, liposomal amphotericin (both Astellas Pharma US, Inc., Northbrook, Ill.), or no antifungal therapy for 12 hours, in 4 technical replicates, with matched media controls exposed to the same conditions. VOCs in the headspace of each vial were extracted onto thermal desorption tubes. Cultures and media samples were incubated at 37° C. at 250 rpm for another 36 hours, with repeat extraction of the headspace gas onto thermal desorption tubes.

Figure 14:
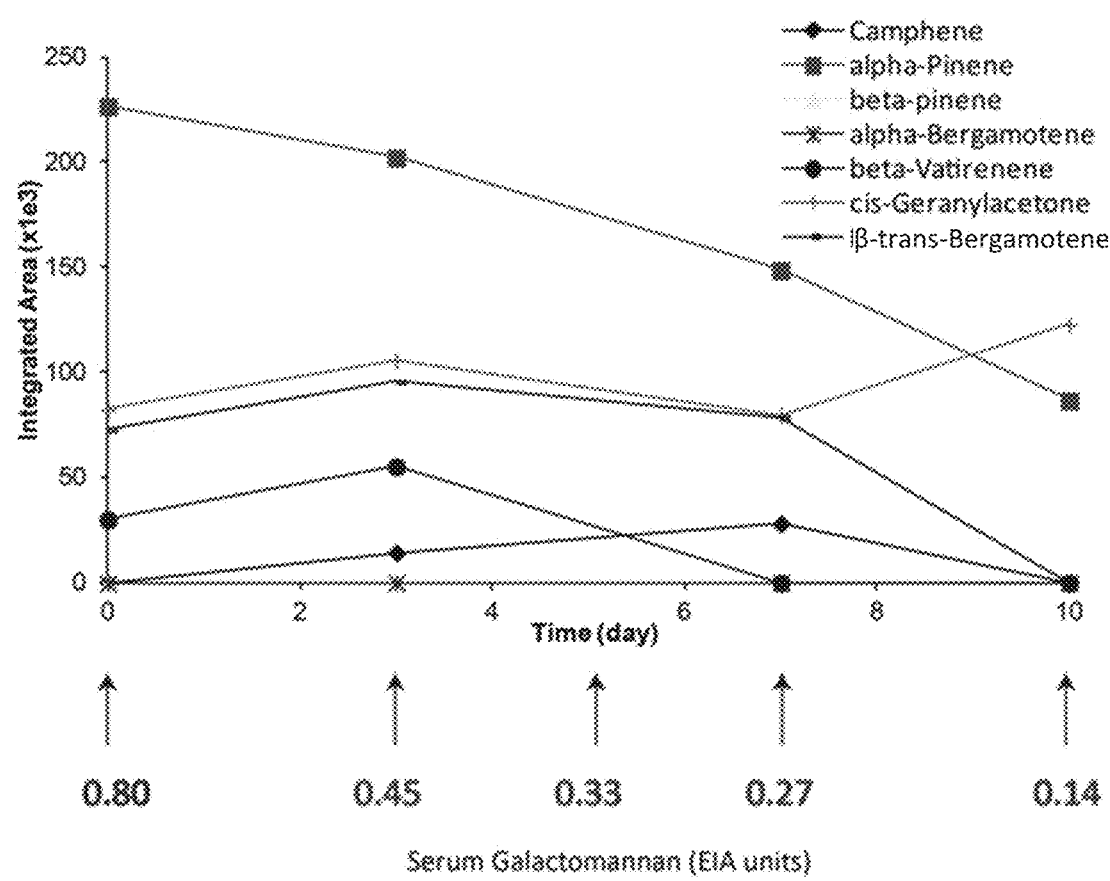
FIG. 14. Attenuation of breath *A. fumigatus* compounds with antifungal therapy.
Figure 20:
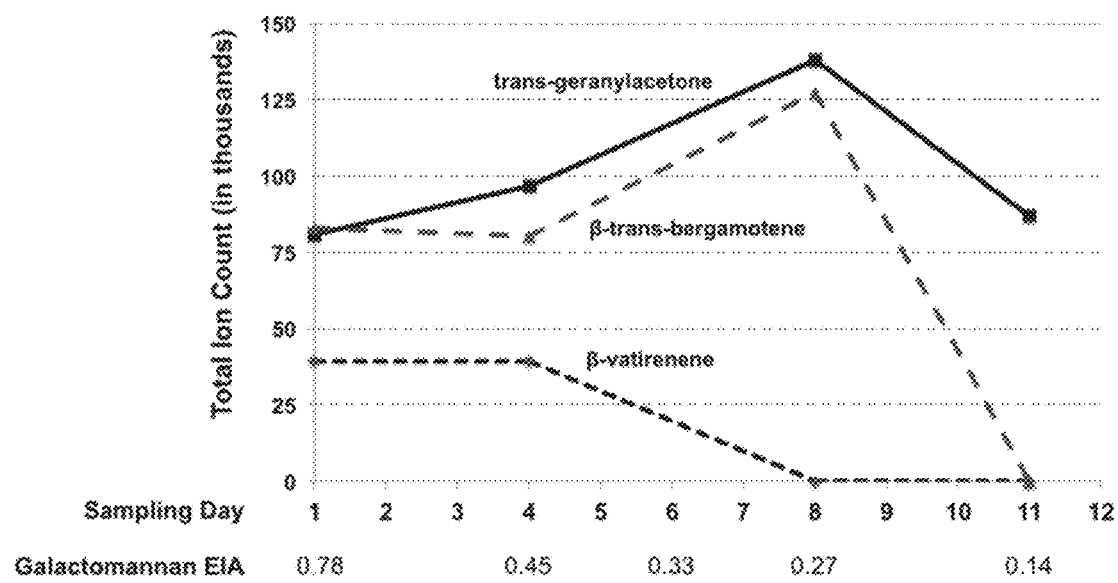
FIG. 20. Example of changes in volatile peak area over time with effective antifungal therapy. Response of the *A. fumigatus* breath metabolite signature to effective antifungal therapy in a patient with invasive aspergillosis. Galactomannan EIA, serum galactomannan enzyme immunoassay index.

As shown in FIGS. 14 and 20, in the patients who were sampled over time, the abundance of the VOC signature declined with effective antifungal therapy, disappearing a few weeks into treatment.

Discussion

We identified distinctive terpene secondary metabolites in the volatile metabolome of the most common pathogenic Aspergilli in vitro, and found that the *A. fumigatus*-specific VOCs β-trans-bergamotene, α-trans-bergamotene, a β-vatirenene-like sesquiterpene, and trans-geranylacetone comprise a fungal metabolic signature that can be used to discriminate patients with IA from patients with other types of pneumonia accurately, in a heterogeneous population at risk for IA. Our results suggest that direct detection of exogenous fungal metabolites in breath, a matrix continuous with the primary site of infection, can be used as a novel, noninvasive, species-specific approach to identifying patients with IA, potentially allowing more precise targeting of antifungal therapy and fewer invasive diagnostic procedures.

While microbial VOC detection in the breath has been suggested for the diagnosis of tuberculosis, *Pseudomonas aeruginosa* pneumonia, and IA,[32] these studies have proposed compounds that are either common primary metabolites or catabolic products of many microbial species or compounds that lack biologically plausible synthetic pathways as biomarkers of disease and are most likely contaminants or artifacts of sample collection.[33] As an example, 2-pentylfuran, a breakdown product of the common fatty acid linoleic acid, was previously proposed as a breath biomarker for IA,[34, 35] but has since been shown to be widely present in food products and ambient air,[35] and not detected in other series[36] or in patient breath samples from our study. Other studies have taken hypothesis-free, pattern-based feature classification approaches to discriminating infected and noninfected patients without identification of the specific biologic components distinguishing these groups, increasing the risk of incorrectly identifying signal in noise and limited reproducibility.[32, 37]

In contrast to these studies, we took a biologically-guided approach to biomarker identification. We identified volatile secondary terpene metabolites released during growth of *A. fumigatus* and were able to modulate secondary metabolite production with various stress conditions and antifungal drug exposure in vitro, suggesting a biologic relationship between the living, metabolically active organism and production of these compounds. Knowledge of these unique terpene metabolites then informed our identification of these fungal secondary metabolites in patient breath samples, and allowed the identification of related compounds such as a β-vatirenene-like sesquiterpene and trans-geranylacetone, potentially reflecting activation of these fungal secondary metabolite pathways, silent under our in vitro culture conditions, in the human lung milieu.

Other groups have previously identified sesquiterpenes in the in vitro volatome of *A. fumigatus*,[36, 38, 39] and one group performed a series identifying a sesquiterpene compound in the breath of 8 IA patients,[36] although the dominant metabolite, β-trans-bergamotene, was misidentified as β-farnesene in these studies, given the similarity in fragmentation patterns of these compounds and the absence of β-trans-bergamotene from the NIST library. In our study, and in a concurrent independent assessment of the in vitro *A. fumigatus* volatome (Drs. Christoph Heddergott and Jean Paul Latgé, personal communication), the NIST library provisionally identified β-trans-bergamotene as β-farnesene. When we spiked a pure β-farnesene standard into a culture of *A. fumigatus* to confirm the identity of this metabolite, the retention time of β-farnesene and our endogenous sesquiterpene were clearly distinct. In contrast, we observed augmentation of this endogenous sesquiterpene with the addition of a β-trans-bergamotene standard, and perfect retention time and spectral pattern alignment with this endogenous sesquiterpene. Interestingly, *A. fumigatus* production of β-trans-bergamotene has been known since at least 1976,[40] although the enzyme that catalyzes the formation of this compound, a cryptic β-trans-bergamotene synthase, was only recently discovered in a secondary metabolite biosynthetic gene cluster.[41] β-trans-bergamotene is putatively a precursor metabolite for fumagillin, a secondary meroterpenoid metabolite with antibiotic and anti-angiogenic properties.[20, 41]

The biologic significance of these sesquiterpene products, whether as end-products themselves or as precursors to other secondary metabolites, and their role in fungal pathogenesis are yet undefined. While not required for primary growth of the organism, a substantial diversion of resources away from primary metabolism is required for synthesis of these secondary metabolites, and many fungal species have evolved unique terpene cyclases with distinctive suites of sesquiterpene products of great structural and stereochemical diversity.[18, 19, 23, 42] These products are believed to have roles in inter- and intraspecies communication, deterring competing microorganisms in the environment and potentially contributing to survival of the organism in the mammalian host.[18, 21-23]

Based on the marked interspecies diversity of sesquiterpene production in vitro, we believe the secondary metabolite signature identified in IA patients in this study is likely specific for *A. fumigatus*, the dominant cause of IA[14]. Other *Aspergillus* species likely have their own distinctive volatile secondary metabolite signatures in vivo. With the advent of galactomannan testing, proven IA cases and cases with species-level *Aspergillus* identification are increasingly rare, but the breath metabolite signature identified all of the galactomannan-positive probable IA cases suggesting *A. fumigatus* as the causative species. *A. flavus, terreus,* or calidoustus were not identified as the causal species of any IA cases at our institution over the study period.

These findings provide proof-of-concept that direct detection of exogenous fungal metabolites in breath can be used as a noninvasive approach to identifying the underlying microbial etiology of pneumonia. GC-MS or real-time gas sensors, e.g., point-of-care, bedside diagnostic tests, can be used to detect IA based on the detection of specific microbial volatile signatures.

In addition, the abundance of the VOC signature declined with effective antifungal therapy, disappearing a few weeks into treatment, as shown in FIGS. 14 and 20.

Results: The monoterpenes camphene, α- and β-pinene, and limonene, and sesquiterpene compounds α- and β-trans-bergamotene were distinctive volatile metabolites of *A. fumigatus* in vitro, distinguishing *A. fumigatus* from other pathogenic Aspergilli. Of 64 patients, 34 were diagnosed with invasive aspergillosis, while 30 were ultimately diagnosed with other causes of pneumonia, including other invasive mycoses. A signature of the sesquiterpene metabolites α-trans-bergamotene and β-trans-bergamotene, a β-vatirenene-like sesquiterpene, and the sesquiterpene intermediate trans-geranylacetone identified patients with invasive aspergillosis with 94% sensitivity (95% confidence interval [CI], 81%-98%) and 93% specificity (95% CI, 79%-98%).

Conclusions and Relevance:

In patients with suspected fungal pneumonia, an *A. fumigatus*-specific secondary metabolite signature in breath can identify individuals with invasive aspergillosis. These results provide proof-of-concept that direct detection of exogenous fungal metabolites in breath can be used as a novel, noninvasive, species-specific approach to identifying the precise microbial cause of pneumonia.

REFERENCES

1. Hammond S P, Marty F M, Bryar J M, DeAngelo D J, Baden L R. Invasive fungal disease in patients treated for newly diagnosed acute leukemia. *American Journal of Hematology.* 2010; 85:695-699.
2. Kontoyiannis D P, Man Ka, Park B J, et al. Prospective surveillance for invasive fungal infections in hematopoietic stem cell transplant recipients, 2001-2006: overview of the Transplant-Associated Infection Surveillance Network (TRANSNET) Database. *Clinical infectious diseases: an official publication of the Infectious Diseases Society of America.* 2010; 50:1091-1100.
3. Singh N, Paterson D L. *Aspergillus* infections in transplant recipients. *Clin Microbiol Rev.* 2005; 18:44-69.
4. Pappas P G, Alexander B D, Andes D R, et al. Invasive fungal infections among organ transplant recipients: results of the Transplant-Associated Infection Surveillance Network (TRANSNET). *Clinical infectious diseases: an official publication of the Infectious Diseases Society of America.* 2010; 50:1101-1111.
5. Neofytos D, Horn D, Anaissie E, et al. Epidemiology and outcome of invasive fungal infection in adult hematopoietic stem cell transplant recipients: analysis of Multicenter Prospective Antifungal Therapy (PATH) Alliance registry. *Clin Infect Dis.* Feb. 1, 2009; 48(3):265-273.
6. Lin S J, Schranz J, Teutsch S M. Aspergillosis case-fatality rate: systematic review of the literature. *Clin Infect Dis.* 2001; 32:358-366.
7. Segal B H. Aspergillosis. *N Engl J Med. Apr.* 30 2009; 360(18):1870-1884.
8. Greene R E, Schlamm H T, Oestmann J W, et al. Imaging findings in acute invasive pulmonary aspergillosis: clinical significance of the halo sign. *Clin Infect Dis.* 2007; 44:373-379.
9. Won H J, Lee K S, Cheon J E, et al. Invasive pulmonary aspergillosis: prediction at thin-section CT in patients with neutropenia—a prospective study. *Radiology.* 1998; 208:777-782.
10. Perfect J R, Cox G M, Lee J Y, et al. The impact of culture isolation of *Aspergillus* species: a hospital-based survey of aspergillosis. *Clin Infect Dis.* 2001; 33:1824-1833.
11. Reichenberger F, Habicht J, Matt P, et al. Diagnostic yield of bronchoscopy in histologically proven invasive pulmonary aspergillosis. *Bone Marrow Transplant.* 1999; 24:1195-1199.
12. Hope W W, Walsh T J, Denning D W. Laboratory diagnosis of invasive aspergillosis. *Lancet Infect Dis.* 2005; 5:609-622.
13. Pfeiffer C D, Fine J P, Safdar N. Diagnosis of invasive aspergillosis using a galactomannan assay: a meta-analysis. *Clin Infect Dis.* 2006; 42:1417-1427.
14. Koo S, Bryar J M, Page J H, Baden L R, Marty F M. Diagnostic performance of the (1→3)-beta-D-glucan assay for invasive fungal disease. *Clin Infect Dis.* Dec. 1 2009; 49(11):1650-1659.
15. Harrison E, Stalhberger T, Whelan R, et al. *Aspergillus* DNA contamination in blood collection tubes. *Diagnostic Microbiology and Infectious Disease.* 2010; 67:392-394.
16. Loeffler J, Hebart H, Bialek R, et al. Contaminations occurring in fungal PCR assays. *Journal of clinical microbiology.* 1999; 37:1200-1202.
17. Mengoli C, Cruciani M, Barnes R A, Loeffler J, Donnelly J P. Use of PCR for diagnosis of invasive aspergillosis: systematic review and meta-analysis. *Lancet Infect Dis.* 2009; 9:89-96.
18. Keller N P, Turner G, Bennett J W. Fungal secondary metabolism—from biochemistry to genomics. *Nat Rev Microbiol.* 2005; 3:937-947.
19. Kramer R, Abraham W-R. Volatile sesquiterpenes from fungi: what are they good for? *Phytochemistry Reviews.* 2012; 11:15-37.
20. Frisvad J C, Rank C, Nielsen K F, Larsen T O. Metabolomics of *Aspergillus fumigatus. Med Mycol.* 2008:1-19.
21. McDonagh A, Fedorova N D, Crabtree J, et al. Subtelomere directed gene expression during initiation of invasive aspergillosis. *PLoS Pathog.* 2008; 4:e1000154.
22. Gershenzon J, Dudareva N. The function of terpene natural products in the natural world. *Nature chemical biology.* 2007; 3:408-414.
23. Cane D E, Kang I. Aristolochene synthase: purification, molecular cloning, high-level expression in *Escherichia coli*, and characterization of the *Aspergillus terreus* cyclase. *Archives of biochemistry and biophysics.* 2000; 376:354-364.
24. Varga J, Houbraken J, Van Der Lee HaL, Verweij P E, Samson Ra. *Aspergillus calidoustus* sp. nov., causative agent of human infections previously assigned to *Aspergillus ustus. Eukaryotic cell.* 2008; 7:630-638.
25. Baddley J W, Marr Ka, Andes D R, et al. Patterns of susceptibility of *Aspergillus* isolates recovered from patients enrolled in the Transplant-Associated Infection Surveillance Network. *Journal of clinical microbiology.* 2009; 47:3271-3275.
26. Balajee S A, Kano R, Baddley J W, et al. Molecular identification of *Aspergillus* species collected for the Transplant-Associated Infection Surveillance Network. *Journal of clinical microbiology.* 2009; 47:3138-3141.
27. Brakhage Aa. Regulation of fungal secondary metabolism. *Nature Reviews Microbiology.* 2013; 11:21-32.
28. Pontecorvo G, Roper J A, Hemmons L M, Macdonald K D, Bufton A W J. The genetics of *Aspergillus nidulans. Advances in genetics.* 1953; 5:141-238.
29. De Pauw B, Walsh T J, Donnelly J P, et al. Revised definitions of invasive fungal disease from the European Organization for Research and Treatment of Cancer/Invasive Fungal Infections Cooperative Group and the National Institute of Allergy and Infectious Diseases Mycoses Study Group (EORTC/MSG) C. *Clin Infect Dis.* 2008; 46:1813-1821.
30. Warnes G, Bolker B, Bonebakker L, Gentleman R, W H A L, Lumley T. gplots: Various R programming tools for plotting data. *The Comprehensive R Archive Network.* 2009:cran.r-project.org/package=gplots.
31. Simel D L, Samsa G P, Matchar D B. Likelihood ratios with confidence: Sample size estimation for diagnostic test studies. *Journal of Clinical Epidemiology.* 1991; 44:763-770.
32. Sethi S, Nanda R, Chakraborty T. Clinical application of volatile organic compound analysis for detecting infectious diseases. *Clinical microbiology reviews.* 2013; 26:462-475.
33. Kwak J, Preti G. Volatile disease biomarkers in breath: a critique. *Curr Pharm Biotechnol. July* 2011; 12(7): 1067-1074.
34. Syhre M, Scotter J M, Chambers S T. Investigation into the production of 2-Pentylfuran by *Aspergillus fumigatus* and other respiratory pathogens in vitro and human breath samples. *Med Mycol.* 2008; 46:209-215.

35. Chambers S T, Bhandari S, Scott-Thomas A, Syhre M. Novel diagnostics: progress toward a breath test for invasive *Aspergillus fumigatus*. *Med Mycol.* 2010.
36. Lin J, Li M, Xu W, et al. Techniques in Infectious Diseases: Identification of Unique Volatile Compounds of *Aspergillus fumigatus* for Potential Diagnostic Breath Test by HS-SPME and GC-MS. *J Immunol Tech Infect Dis.* 2013:9-12.
37. Baggerly K A, Morris J S, Edmonson S R, Coombes K R. Signal in noise: evaluating reported reproducibility of serum proteomic tests for ovarian cancer. *J Natl Cancer Inst. Feb.* 16 2005; 97(4):307-309.
38. Fiedler K, Schutz E, Geh S. Detection of microbial volatile organic compounds (MVOCs) produced by moulds on various materials. *Int J Hyg Environ Health.* 2001; 204:111-121.
39. Bazemore R A, Feng J, Cseke L, Podila G K. Biomedically important pathogenic fungi detection with volatile biomarkers. *Journal of breath research.* 2012; 6:016002.
40. Nozoe S, Kobayashi H, Morisaki N. Isolation of b-trans-bergamotene from *Aspergillus fumigatus*, a fumagillin producing fungi. *Tetrahedron Letters.* 1976; 50:4625-4626.
41. Lin H-C, Chooi Y-H, Dhingra S, Xu W, Calvo A M, Tang Y. The fumagillin biosynthetic gene cluster in *Aspergillus fumigatus* encodes a cryptic terpene cyclase involved in the formation of β-trans-bergamotene. *Journal of the American Chemical Society.* 2013; 135:4616-4619.
42. Christianson D W. Chemistry. Roots of biosynthetic diversity. *Science.* 2007; 316:60-61.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of treating a subject who has invasive aspergillosis (IA), the method comprising:
    obtaining a sample comprising breath of a subject or headspace from a culture suspected of comprising *Aspergillus* isolated from a subject;
    detecting the presence in the sample at least two or more VOCs selected from the group consisting of camphene, α-pinene, β-pinene, limonene, α-trans-bergamotene, β-trans-bergamotene, and trans-geranylacetone; and
    administering an antifungal treatment to the subject who has at least two or more of camphene, α-pinene, β-pinene, limonene, α-trans-bergamotene, β-trans-bergamotene, and trans-geranylacetone.
2. The method of claim 1, wherein the treatment comprises administration of one or more doses of one or more antifungal compounds.
3. A method of monitoring efficacy of a treatment for invasive aspergillosis (IA) in a subject, the method comprising:
    determining a first level of at least two or more volatile organic compounds (VOCs) produced by the *Aspergillus* species in a sample comprising breath from the subject or headspace from a culture suspected of comprising *Aspergillus* isolated from the subject, wherein the VOCs are selected from the group consisting of camphene, α-pinene, β-pinene, limonene, α-trans-bergamotene, β-trans-bergamotene, trans-geranylacetone, elixene, alpha-santalene, beta-elemene, acoradien, chamigrene, 1,5,9-trimethyl cyclododecatriene, 9-decene-2-one and beta-sesquiphellandrene, in the subject;
    administering a treatment for IA to the subject;
    determining a second level of the VOCs in a sample obtained after administration of the treatment to the subject; and
    comparing the first and second levels of VOCs, wherein a decrease in the VOCs indicates that the treatment has been effective in treating the IA in the subject, and an increase or no change indicates that the treatment has not been effective in treating the IA in the subject.
4. The method of claim 3, wherein the treatment comprises administration of one or more doses of one or more antifungal compounds.
5. A method of identifying a candidate compound for the treatment of invasive aspergillosis (IA) in a subject, the method comprising:
    providing a test culture suspected of comprising one or more *Aspergillus* species from the subject;
    detecting a baseline level of at least two or more fungal VOCs in headspace obtained from the test culture in the absence of the test compound, wherein the VOCs are selected from the group consisting of camphene, α-pinene, β-pinene, limonene, α-trans-bergamotene, β-trans-bergamotene, trans-geranylacetone, elixene, alpha-santalene, beta-elemene, acoradien, chamigrene, 1,5,9-trimethyl cyclododecatriene, 9-decene-2-one and beta-sesquiphellandrene, in the subject;
    contacting the test culture with a test compound;
    determining a second level of the VOCs in the test culture;
    comparing the second level of VOCs to the baseline level; and
    identifying a test compound that decreases levels of fungal VOCs in the test culture as a candidate compound for the treatment of IA.
6. The method of claim 1, wherein determining the presence of a VOC comprises assaying the sample to detect the presence the VOC.
7. The method of claim 6, wherein assaying the sample to detect the presence the VOC comprises using a gas chromatography (GC) or spectrometry method.
8. The method of claim 7, wherein the spectrophotometry method is mobility spectrometry (IMS) or differential mobility spectrometry (DMS).
9. The method of claim 1, wherein the subject is a human.
10. The method of claim 2, wherein the antifungal compound is an amphotericin B formulation; an azole antifungal compound; or an echinocandin antifungal compound.

* * * * *

UNITED STATES PATENT AND TRADEMARK OFFICE
CERTIFICATE OF CORRECTION

PATENT NO. : 11,692,212 B2
APPLICATION NO. : 17/228382
DATED : July 4, 2023
INVENTOR(S) : Sophia Koo et al.

It is certified that error appears in the above-identified patent and that said Letters Patent is hereby corrected as shown below:

In the Claims

In Column 28, Line 49, Claim 6, before "the" insert -- of --

In Column 28, Line 51, Claim 7, before "the" insert -- of --

Signed and Sealed this
Twenty-ninth Day of August, 2023

*Katherine Kelly Vidal*
Katherine Kelly Vidal
*Director of the United States Patent and Trademark Office*